United States Patent [19]

Alvarado et al.

[11] Patent Number: 5,391,757

[45] Date of Patent: Feb. 21, 1995

[54] BENZENESULFONYL CARBOXAMIDE COMPOUNDS INTERMEDIATE COMPOUNDS AND METHODS OF PREPARATION THEREOF AND USE OF SAID COMPOUNDS AND INTERMEDIATE COMPOUNDS AS HERBICIDAL AGENTS

[75] Inventors: Sergio I. Alvarado, Princeton; Alvin D. Crews, Jr., Plainsboro; Peter J. Wepplo, Princeton; Robert F. Doehner, Jr., East Windsor; Thomas E. Brady, Whitehouse Station; David M. Gange, Princeton; Desiree L. Little, Burlington, all of N.J.

[73] Assignee: American Cyanamid Company, Wayne, N.J.

[21] Appl. No.: 243,680

[22] Filed: May 9, 1994

Related U.S. Application Data

[60] Division of Ser. No. 87,952, Jul. 6, 1993, Pat. No. 5,338,883, which is a division of Ser. No. 856,262, Mar. 23, 1992, Pat. No. 5,252,539, which is a division of Ser. No. 611,626, Nov. 13, 1990, Pat. No. 5,120,854, which is a division of Ser. No. 417,400, Oct. 5, 1989, Pat. No. 4,992,094, which is a division of Ser. No. 214,507, Jul. 7, 1988, Pat. No. 4,883,914, which is a continuation-in-part of Ser. No. 806,416, Aug. 17, 1987, abandoned.

[51] Int. Cl.$^6$ ............... C07D 233/70; C07D 233/72; C07D 263/32
[52] U.S. Cl. ............... 548/228; 548/316.4; 548/316.7; 548/317.1
[58] Field of Search ............... 548/228, 316.4, 316.7, 548/317.1

[56] References Cited

U.S. PATENT DOCUMENTS

| 3,432,507 | 3/1969 | Paquette | 548/301 |
| 4,132,786 | 1/1979 | Moreau et al. | 548/301 |
| 4,218,238 | 8/1980 | Taylor et al. | 548/301 |
| 4,404,012 | 9/1983 | Orwick et al. | 548/301 |

OTHER PUBLICATIONS

CA 118:7341a A new general . . . δ–amino acids. Obrecht et al., p. 782, 1993.
Chemical Abstracts, vol. 53, No. 9, Abstract 9115(b–d), May 10, 1959.
Chemical Abstracts, vol. 54, No. 17, Abstract 18378–79, Sep. 10, 1960.
Chemical Abstracts vol. 95, No. 17, Abstract 144,568a, Oct. 26, 1981, p. 109.
Chemical Abstracts, vol. 98, No. 1, Abstract 188r, Jan. 3, 1983, p. 190.
CA III(15):133 763h Herbicidal . . . intermediates. Alvarado et al., p. 720, 1989.
CA 112(13):1184272g (Aminodcyl)phenylsulfonamides and herbicides containing them. Takeuchi et al., p. 701, 1990.
CA113 (II):97205h Preparation of . . . agents. Alvarado et al., p. 670, 1990.

Primary Examiner—Mary C. Lee
Assistant Examiner—Joseph K. McKane
Attorney, Agent, or Firm—Michael P. Morris

[57] ABSTRACT

There are provided novel benzenesulfonyl carboxamide compounds and novel intermediate benzenesulfonyl-2-imidazolin-5-one compounds, novel intermediates and methods for the preparation of said compounds, and a method for controlling a variety of annual and perennial plant species utilizing novel benzenesulfonyl carboxamide compounds and novel intermediate benzenesulfonyl 2-imidazolin-5-one compounds.

3 Claims, No Drawings

BENZENESULFONYL CARBOXAMIDE COMPOUNDS INTERMEDIATE COMPOUNDS AND METHODS OF PREPARATION THEREOF AND USE OF SAID COMPOUNDS AND INTERMEDIATE COMPOUNDS AS HERBICIDAL AGENTS

This is a divisional of application(s) Ser. No. 08/087,952, filed on Jul. 6, 1993, now U.S. Pat. No. 5,338,883, which is a divisional of application Ser. No. 07/856,262, filed on Mar. 23, 1992, now U.S. Pat. No. 5,252,539, issued Oct. 12, 1993, which is a divisional of application Ser. No. 07/611,626, filed on Nov. 13, 1990, now U.S. Pat. No. 5,120,854, issued Jun. 9, 1992, which is a divisional of application Ser. No. 07/417,400, filed Oct. 5, 1989, now U.S. Pat. No. 4,992,094, issued Feb. 12, 1991, which is a divisional of application Ser/ No. 07/214,507, filed Jul. 7, 1988, now U.S. Pat. No. 4,883,914, issued Nov. 28, 1989, which in turn, is a continuation-in-part of application Ser. No. 07/806,416, filed Aug. 17, 1987, abandoned.

SUMMARY OF THE INVENTION

The invention is directed to certain herbicidal intermediate benzenesulfonyl 2-imidazolin-5-one compounds of formula (I) and certain herbicidal benzenesulfonyl carboxamide compounds of formula (II)

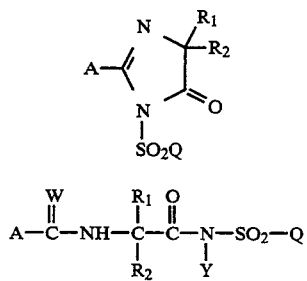

wherein
A in both formula (I) and (II) is hydrogen;
straight or branched $C_1$-$C_4$ alkyl, optionally substituted with one to three halogens, $C_1$-$C_4$ alkoxy, $C_1$-$C_4$ alkylthio, $C_1$-$C_4$ alkylsulfinyl, $C_1$-$C_4$ alkylsulfonyl, carboalkoxy, phenyl, or oxo;
straight or branched $C_1$-$C_4$ alkenyl, optionally substituted with one to three halogens or phenyl;
$C_1$-$C_4$ alkynyl, optionally substituted with one to three halogens;
and additionally in formula (II) A is amino, optionally substituted with straight or branched $C_1$-$C_6$ alkyl, $C_3$-$C_6$ cycloalkyl, $C_1$-$C_4$ haloalkyl, straight or branched $C_1$-$C_6$ alkenyl, $C_3$-$C_6$ cycloalkenyl, phenyl, benzyl,(di)alkylamino, or $C_1$-$C_4$ alkoxy;
$C_1$-$C_4$ alkoxy; or
$C_1$-$C_4$ alkylthio;
$R_1$ is $C_1$-$C_4$ alkyl;
$R_2$ is $C_1$-$C_4$ alkyl or $C_3$-$C_6$ cycloalkyl; and when $R_1$ and $R_2$ are taken together with the carbon to which they are attached, they may be $C_3$-$C_6$ cycloalkyl optionally substituted with methyl;
and when $R_1$ and $R_2$ are not the same, thus creating an asymmetric center, the optical isomers thereof;
Q is represented by formula (III)

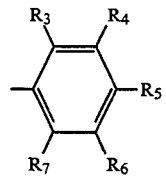

wherein
$R_3$-$R_7$ are each hydrogen; halogen; nitro; cyano;
straight or branched $C_1$-$C_4$ alkyl, optionally substituted with one or more halogens or phenyl;
straight or branched $C_1$-$C_4$ alkenyl, optionally substituted with one to three halogens;
$OR_8$ where $R_8$ is hydrogen; $C_1$-$C_4$ alkyl, optionally substituted with halogen(s), $C_1$-$C_4$ alkoxy, or phenyl; or $C_1$-$C_4$ alkenyl optionally substituted with one to three halogens or phenyl;
phenyl, optionally substituted with one to three halogens, one to three $C_1$-$C_4$ alkyl, one to three $C_1$-$C_4$ alkoxy or one to two nitro;
$C_1$-$C_4$ alkylcarbonyl, optionally substituted with halogen (s);
$C_1$-$C_4$ alkylthio, optionally substituted with halogen (s);
$C_1$-$C_4$ alkylsulfinyl, optionally substituted with halogen(s);
$C_1$-$C_4$ alkylsulfonyl, optionally substituted with halogen (s);
amino, optionally substituted by $C_1$-$C_4$ alkyl;
$CO_2R_9$ where $R_9$ is hydrogen, $C_1$-$C_4$ alkyl, optionally ally substituted with one to three halogens;
$R_3$-$R_4$, $R_4$-$R_5$, $R_5$-$R_6$, $R_6$-$R_7$ may also be —(CH=CH—CH=CH)— which may also be optionally substituted with up to three of the substituents described for $R_3$-$R_7$ above;
with the proviso that no more than three of $R_3$-$R_7$ can be: cyano, nitro, (substituted)phenyl, alkylcarbonyl, alkylthio, alkylsulfinyl, alkylsulfonyl, amine, $CO_2R_9$;
W is O or S;
Y is hydrogen; or a salt thereof, wherein Y is a cation.

DESCRIPTION OF THE PREFERRED EMBODIMENTS

A preferred group of benzenesulfonyl carboxamides and benzenesulfonyl-2-imidazolin-5-one compounds of formula II and formula I above are those wherein
A is hydrogen or methyl;
$R_1$ is methyl;
$R_2$ is isopropyl;
$R_3$-$R_7$ are each halogen(s) and/or $C_1$-$C_4$ alkyl, optionally substituted with halogen;
Y is hydrogen, or a cation of alkali metals, alkaline earth metals, manganese, copper, iron,
zinc, cobalt, lead, silver, nickel, ammonium and organic ammonium.

In formula (II) above, alkali metals include: sodium, potassium and lithium, but sodium is generally preferred. Further, the term "organic ammonium" is defined as a group consisting of a positively charged nitrogen atom joined to from one to four groups, each containing from one to 20 carbon atoms. Among the organic ammonium groups which are illustrative for the preparation of the organic ammonium salts of the formula (II) phenylsulfonyl carboxamide herein are: monoalkylammonium, dialkylammonium, trialkylammonium, tetraalkylammonium, monoalkenylammonium, dialkenylammonium, trialkenylammonium, monoalkynylammonium, dialkynylammonium, trialkynylammonium, monoalkanolammonium, dialkanolammonium, trialkanolammonium, $C_3$–$C_6$ cycloalkylammonium, piperidinium, morpholinium, pyrrolidinium, benzylammonium and equivalents thereof. Exemplary of halogen hereinabove are chlorine, fluorine, bromine, and iodine, but chlorine, bromine and fluorine are preferred.

A more preferred group of formula (I) and formula (II) compounds are those wherein A is methyl;

$R_1$ is methyl;

$R_2$ is isopropyl;

$R_3$ is hydrogen, halogen or methyl;

$R_5$ is halogen or methyl, and

W is oxygen.

As indicated above, the present invention relates to novel formula (II) herbicidal benzenesulfonyl carboxamide compounds and novel formula (I) benzenesulfonyl-2-imidazolin-5-one compounds which can serve as intermediates for the preparation of said formula (II) compounds and, additionally, are themselves herbicidal. Thus benzenesulfonyl carboxamide compounds of formula (II) are readily prepared by treatment of compounds of formula (I) with water optionally in the presence of catalytic amounts of an acid, in an inert solvent as illustrated in flow diagram I below.

FLOW DIAGRAM I

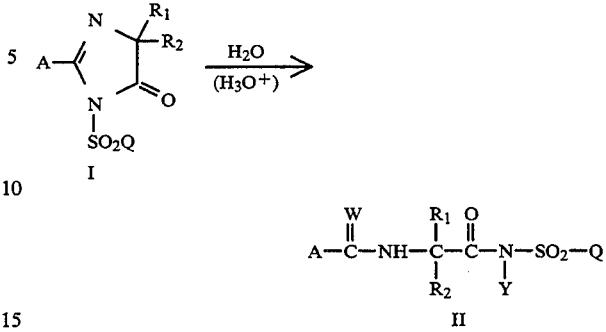

wherein A, $R_1$, $R_2$ and Q are as described above, W is oxygen and Y is hydrogen.

Compounds of formula I for use in the above reaction may conveniently be prepared by the reaction of an α-aminoamide of formula (IV) with a carboxylic acid anhydride of formula (V) (or acid chloride or equivalent thereof), in an inert solvent, optionally in the presence of an acid acceptor to yield a formula (VI) 2-acetamido-2,3-disubstituted amide which may be cyclized by treatment with aqueous alkali to yield imidazolinones of formula (VII). Alternatively imidazolinones of formula (VII) may be prepared directly by the reaction of a formula (IV) e-aminoamide with an ortho ester of formula VIII at elevated temperature in an inert solvent. Imidazolinones of formula (I) may then be obtained by treatment of the thus obtained formula (VIII) imidazolinone with a benzenesulfonyl chloride of formula (IX) in an inert solvent in the presence of an acid acceptor such as triethylamine, pyridine, sodium hydride or the like, and isolation of the desired formula (I) product by careful exclusion of water in the workup. These reactions are illustrated in flow diagram (II) below.

FLOW DIAGRAM II

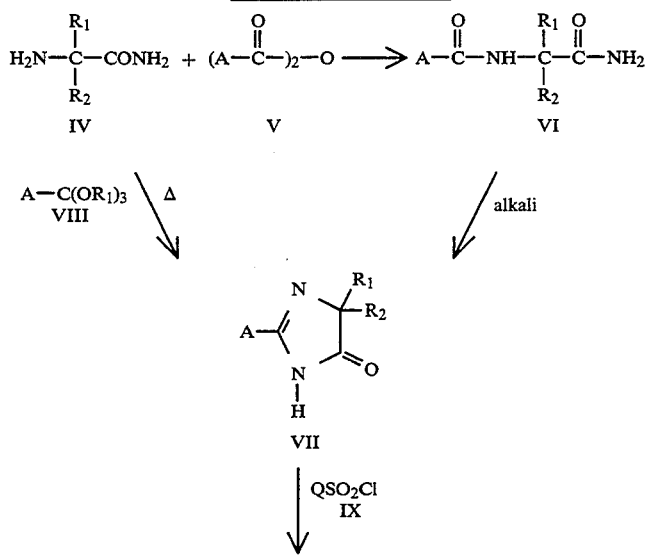

FLOW DIAGRAM II

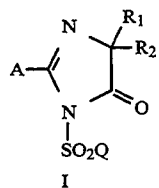
I wherein
A is hydrogen; $C_1$-$C_4$ alkyl; $C_1$-$C_4$ alkenyl; or $C_1$-$C_4$ alkynyl each of which may be optionally substituted as described above for formula (I) and (II), and $R_1$, $R_2$ and Q are as described for formula (I) and (II) above.

Compounds of formula (II) may also be prepared by hydrolysis of compounds of formula II where A is hydrogen with aqueous acid, for example aqueous HCl, which may be isolated as 2-amino-2,3-dialkyl-N-(benzenesulfonyl)carboxamide acid salts (i.e. hydrochlorides) of formula (X) or as their corresponding free bases which exist as zwitterions of formula (XI). The resulting formula (X) or formula (XI) compound upon reaction with a carboxylic acid anhydride of formula (V) or carboxylic acid chloride (or equivalent thereof) or isocyanate of formula XII in an inert solvent (optionally in the presence of an acid acceptor) also yields compounds of formula (II) as illustrated in flow diagram (III) below.

FLOW DIAGRAM III

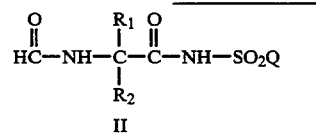
II

↓ aqueous acid (eg HCl)

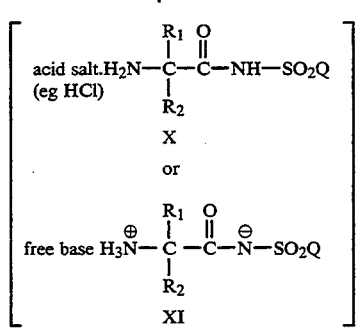

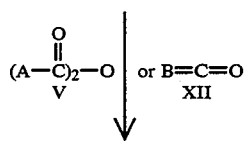
↓

-continued
FLOW DIAGRAM III

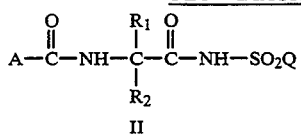
II wherein B is
(substituted) imino, substituted with straight or branched $C_1$-$C_6$ alkyl, $C_3$-$C_6$ cycloalkyl, $C_1$-$C_4$ haloalkyl, straight or branched $C_1$-$C_6$ alkenyl, $C_3$-$C_6$ cycloalkenyl, or phenyl, benzyl, (di)alkylamino or $C_1$-$C_4$ alkoxy.

Another method for the preparation of formula (II) benzenesulfonyl carboxamide compounds of the invention involves the sequential reaction of a formula (VI) 2-acetamido-2,3-disubstituted amide with sodium hydride followed by reaction with a formula (IX) benzenesulfonyl chloride in an inert solvent in a temperature range of about 20° C. to reflux as illustrated in flow diagram (IV) below.

FLOW DIAGRAM IV

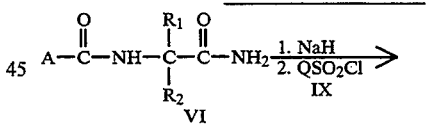

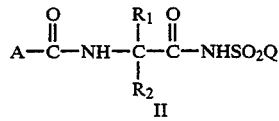
II wherein A, $R_1$, $R_2$ and Q are as described for formula (II above).

Formula (II) benzenesulfonyl carboxamides may also be obtained by reaction of an e-amino acid of formula (XIII) with a carboxylic acid anhydride of formula (V) followed by reaction of the thus-formed formula (XIV) N-acylamino acid with either a dehydrating agent (such as a formula (V) anhydride or dicyclohexylcarbodiimide) to give azlactone XVb, or reaction with an acylating reagent such as an alkylchloroformate to give a mixed anhydride XVa; the "activated" N-acylamino acids (XVa or XVb) are then reacted with an alkali metal salt of a benzenesulfonamide of formula (XVI) to afford, on acidification, compounds of formula (II) as illustrated in flow diagram (V) below.

FLOW DIAGRAM V

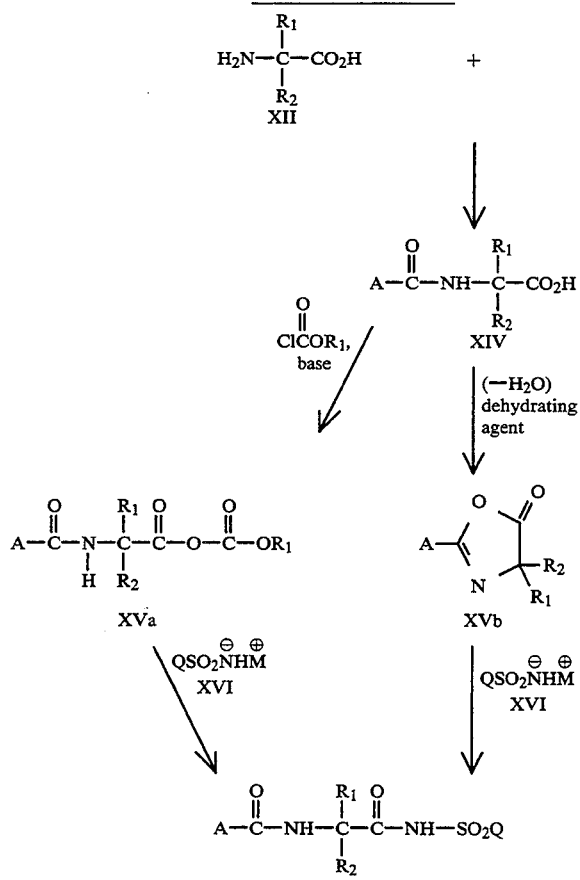

wherein A, $R_1$, $R_2$ and Q are as described above for formula (II), and M is an alkali metal.

Another method for the preparation of formula (II) benzenesulfonyl carboxamides involves the reaction of hydantoin compounds of formula (XVII) with benzenesulfonyl chlorides of formula (IX) in the presence of an acid acceptor such as triethylamine, pyridine, sodium hydride or the like, in an inert organic solvent to yield sulfonyl hydantoins of formula (XVIII). Formula (II) benzenesulfonylcarboxamide compounds of the invention may then be obtained by reaction of formula (XVIII) hydantoins with nucleophiles of formula (XIX) as illustrated in flow diagram VI below.

FLOW DIAGRAM VI

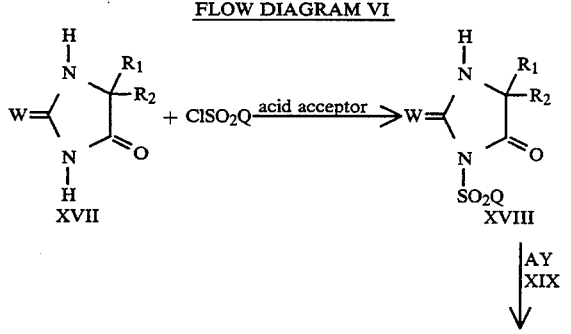

-continued
FLOW DIAGRAM VI

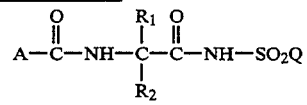

wherein A is amino, alkoxy or alkylthio which may optionally be substituted as described for formula (II); and $R_1$, $R_2$, Q and Y are as described by formula (II) above.

Salts of the benzenesulfonyl carboxamide compounds of this invention may readily be prepared by reaction of a compound of formula (II) where Y is hydrogen with a base such as ammonia, an organic ammonium compound, an alkali or alkaline earth metal hydride or the like in an inert organic solvent as illustrated in flow diagram (VII) below.

FLOW DIAGRAM VII

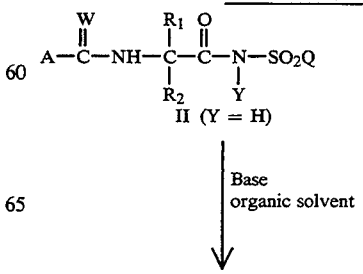

-continued
FLOW DIAGRAM VII

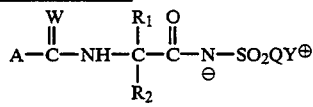

wherein A, $R_1$, $R_2$, Q, W and Y are as previously described for formula (II).

The present invention includes novel formula (VI) 2-acetamido-2,3-disubstituted amide, formula (VII) imidazolinone, formula (X) 2-amino-2,3-dialkyl-N(benzenesulfonyl)carboxamide, formula (XI) zwitterion, formula (XVb) oxazolinone, formula (XVII) hydantoin and formula (XVIII) benzenesulfonyl hydantoin, compounds as described above in the flow diagrams which are intermediates useful for the preparation of novel formula (I) and novel formula (II) herbicidal compounds.

The formula (I) benzenesulfonyl-2-imidazolinone and formula (II) benzenesulfonyl carboxamide compounds of the present invention are effective herbicidal agents useful for the control of a wide variety of annual and perennial monocotyledonous and dicotyledonous plants. These compounds may be applied to the foliage thereof or to soil or water containing seeds or other propagating organs of said plants such as tubers, rhizomes or stolons, at rates of from about 0.032 to 4.0 kg/ha, and preferably at rates from about 0.5 to 2.0 kg/ha.

Rates of application above the 4.0 kg/ha level may be used to effectively kill undesirable plant species. However, rates of application of toxicant in excess of the level necessary to kill the undesirable plants may be is costly and serve no useful function in the environment.

Among the plants which may be controlled with the compounds of this invention are: Helianthus annuus, Sesbania exaltata, Sinapis arvensis, Abutilon theophrasti, Brassica napus, Ambrosia artemisifolia, Xanthium strumarium, Matricaria inodora, Chenopodium album, Amaranthus retroflexus, Cirsium arvense, Datura stramonium, Ipomoea hederacea, Sida spinosa, Portulaca oleracea, Stellaria media, Calystegia sepium, Solanum carolinense, Gallium aparine, Cassia obtusifolia.

It has also been found that many of the formula (I) and formula (II) compounds of the invention are selective herbicides when applied to the foliage of plants or to soil containing seeds of said plants at relatively low rates of application, i.e., at from 0.032 to about 2.0 kg per hectare, depending on the compound used and crop treated.

In particular many of the formula (I) and formula (II) compounds of the invention have been found suitable for the control of undesirable broadleaf weeds in the presence of agronomically important crops such as corn, wheat, barley, soybeans, peanuts and the like.

Formula (II) wherein Y is a salt-forming cation, which are water soluble, can simply be dispersed in water and applied as a dilute aqueous spray to the foliage of plants or to soil containing propagating organs thereof. These salts also lend themselves to formulation as flowable concentrates. While those salts which are soluble in organic solvents, for example organic ammonium salts may be formulated as emulsifiable concentrates, suspension concentrates and the like.

The formula (I) and formula (II) compounds can also be formulated as wettable powders, flowable concentrates, emulsifiable concentrates, granular formulations and the like.

Wettable powders can be prepared by grinding together about 20% to 45% by weight of a finely divided carrier such as kaolin, bentonite, diatomaceous earth, attapulgite, or the like, about 45% to 80% by weight of the active compound, about 2% to 5% by weight of a dispersing agent such as sodium lignosulfonate, and about 2% to 5% by weight of a nonionic surfactant, such as octylphenoxy polyethoxy ethanol, nonylphenoxy polyethoxy ethanol or the like.

A typical flowable liquid can be prepared by admixing about 40% by weight of the active ingredient with about 2% by weight of a gelling agent such as bentonite, about 3% by weight of a dispersing agent such as sodium lignosulfonate, about 1% by weight of polyethylene glycol and about 54% by weight of water.

A typical emulsifiable concentrate can be prepared by dissolving about 5% to 25% by weight of the active ingredient in about 65% to 90% by weight of N-methylpyrrolidone, isophorone, butyl cellosolve, methylacetate or the like and dispersing therein about 5% to 10% by weight of a nonionic surfactant such as an alkylphenoxy polyethoxy alcohol. This concentrate is dispersed in water for application as a liquid spray.

When the compounds of the invention are to be used as herbicides where soil treatments are involved, the compounds may be prepared and applied as granular products. Preparation of the granular product can be achieved by dissolving the active compound in a solvent such as methylene chloride, N-methylpyrrolidone or the like and spraying the thus prepared solution on a granular carrier such as corncob grits, sand, attapulgite, kaolin or the like.

The granular product thus prepared generally comprises about 3% to 20% by weight of the active ingredient and about 97% to 80% by weight of the granular carrier.

In order to facilitate a further understanding of the invention, the following non-limiting examples are presented primarily for the purpose of illustrating certain more specific details thereof. Unless otherwise noted, all parts are by weight.

EXAMPLE 1

Preparation of 2-N-acetyl-2,3-dimethylbutyramide

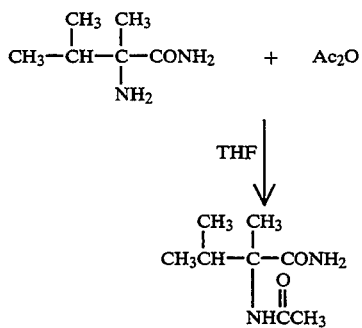

2-Amino-2,3-dimethylbutyramide (114.8 g, 0.88 mols) is added to a stirred solution of 120 mL of acetic anhydride in 200 mL of THF cooled to −20° C. under nitrogen at such a rate that temperature remains at −20° C. Upon completion of the addition the reaction mixture is allowed to warm to room temperature and then stir for 18 hours. The title product precipitates as a white solid, which is filtered off and washed with ether to yield 140.2 g of 2-N-acetyl-2,3-dimethylbutyramide having amp of 114°-118° C.

EXAMPLE 2

Preparation of 2,4-dimethyl-4-isopropyl-1,3-imidazolin-5-one

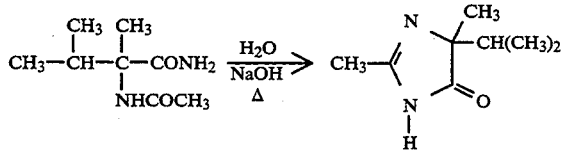

2-N-Acetyl-2,3-dimethylbutyramide (70 g) in 600 mL of aqueous NaOH (10%) is heated at 60°-70° C. (under N2) for two hours. The reaction mixture is cooled with ice, and the pH adjusted to 5, first with conc. HCl and then with 10% HCl. The acidified solution is extracted with ethyl acetate several times affording 46 g of the title product after removal of the solvent. Concentration of the mother liquors by evaporation and extraction with ethyl acetate affords an additional 9.9 g of product. The isolated 2,4-dimethyl-4-isopropyl-1,3-imidazolin-4-one has a mp 107°-109° C.

EXAMPLE 3

Preparation of 5-methyl-5-isopropyl-1,3-imidazolin-4-one

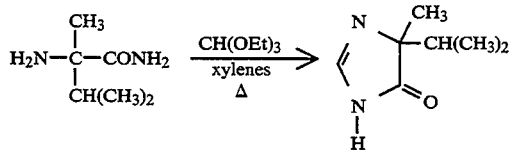

A solution of 2-amino-2,3-dimethylbutyramide (130 g, 1 mol) and triethylorthoformate (183 mL 1.1 mol) in 850 mL Of xylenes is heated to reflux using mechanical stirring, and a Dean-Stark trap to collect ethanol. After three hours and 30 minutes no more ethanol is eliminated, and the reaction mixture is allowed to attain 50° C. The mixture is concentrated to ⅓ of the volume and is then allowed to stand for 18 hours. The title product precipitates as a white solid which is collected by filtration (119.6 g), having mp 101°-104° C.

EXAMPLE 4

Preparation of 2,4-dimethyl-4-isopropyl-1,3-imidazolin-5-one

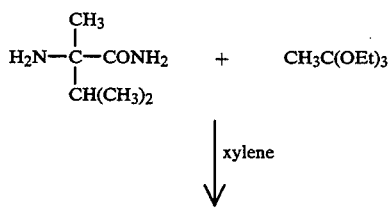

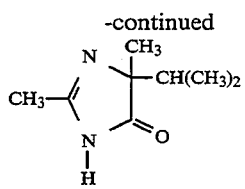

A solution of 2-amino-2,3-dimethylbutyramide (100 g) and triethylorthoacetate (125 g) in xylenes (500 mL) is heated at reflux (105°-138° C.) under a Dean-Stark trap. After six hours, 200 mL distillate is collected at a pot temperature of 138° C. and only xylene was present in the distillate. The reaction mixture is cooled and concentrated in vacuo to 150 g thick light yellow oil. Hexanes is added and the resulting solid filtered off to yield the 96.7 g (81.6%) of the title product having mp 107°-110° C.

Utilizing the above procedure and substituting (S)-2-amino-2,3-dimethylbutyramide (m.p. 78°-80° C. $[\alpha]_D^{25} -71°$ (THF)) affords (S)-2,4-dimethyl-4-isopropyl-1,3-imidazolin-5-one, m.p. 93°-97° C., $[\alpha]_D^{25} -53°$ (THF).

EXAMPLE 5

Preparation of 1-(n-methylbenzenesulfonyl)-2,4-dimethyl-4-isopropyl-1,3-imidazolin-5-one

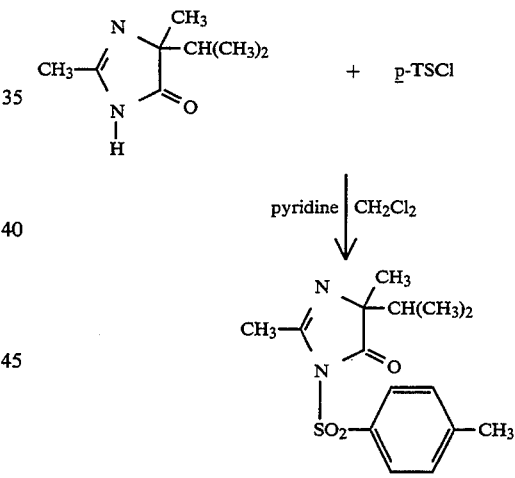

p-Toluenesulfonyl chloride (2.47 g, 12.97 mol) is added to a stirred solution of 2,4-dimethyl-4-isopropyl-1,3-imidazolin-5-one (2 g, 12.97 mol) in 40 mL of dry methylene chloride and 1.4 molar equivalents of dry pyridine, cooled with an ice bath and under nitrogen. The reaction mixture is allowed to warm to room temperature and then stir for 16 hours. The reaction mixture is rapidly washed twice with water, once with HCl 10%, once with water, and dried over $Na_2SO_4$. Evaporation of the methylene chloride solution affords 2.97 g of a yellow oil, which is purified using a silica gel column eluting with $CH_3CN$/hexanes/$CH_2Cl_2$ (1:3:6) yielding 1.95 g of solid; recrystallization from $CH_2C_2$/ether/hexanes affords 1.37 g of the title product as a white solid, having mp 78°-80° C.

Utilizing the above procedure yields the formula I compounds listed in Table I below.

TABLE I

A−C(=N−)−C(R₁)(R₂)−C(=O)−N(SO₂Q)−  (structure shown at top)

| Example | A | Q | R₁ | R₂ | mp °C. |
|---|---|---|---|---|---|
| 5a | CH₃ | 4-CH₃-C₆H₄ | CH₃ | i-C₃H₇ | 78–80 |
| 5b | CH₃ | 4-Cl-C₆H₄ | CH₃ | i-C₃H₇ | 82–83.5 |
| 5c | CH₃ | 2,4-(NO₂)₂-C₆H₃ | CH₃ | i-C₃H₇ | 159–160 |
| 5d | CH₃ | 2,4-Cl₂-5-CH₃-C₆H₂ | CH₃ | i-C₃H₇ | 121–123 |
| 5e | CH₃ | 3-Cl-4-F-C₆H₃ | CH₃ | i-C₃H₇ | 96–98 |
| 5f | CH₃ | 3,4-diCH₃-Cl-C₆H₃ | CH₃ | i-C₃H₇ | 85–86 |
| 5g | CH₃ | 2,6-Cl₂-C₆H₃ (with CH₃) | CH₃ | i-C₃H₇ | 115–118 |
| 5h | CH₃ | 3-CH₃-4-Cl-C₆H₃ | CH₃ | i-C₃H₇ | 103–104 (S)−(−) [α]$_D^{25}$ = −36.41 |
| 5i | CH₃ | 2,4-Cl₂-C₆H₃ | CH₃ | i-C₃H₇ | 123–125 |

EXAMPLE 6

Preparation of 2-acetamido-2,3-dimethyl-N-(D-toluenesulfonyl)-butyramide-Method A

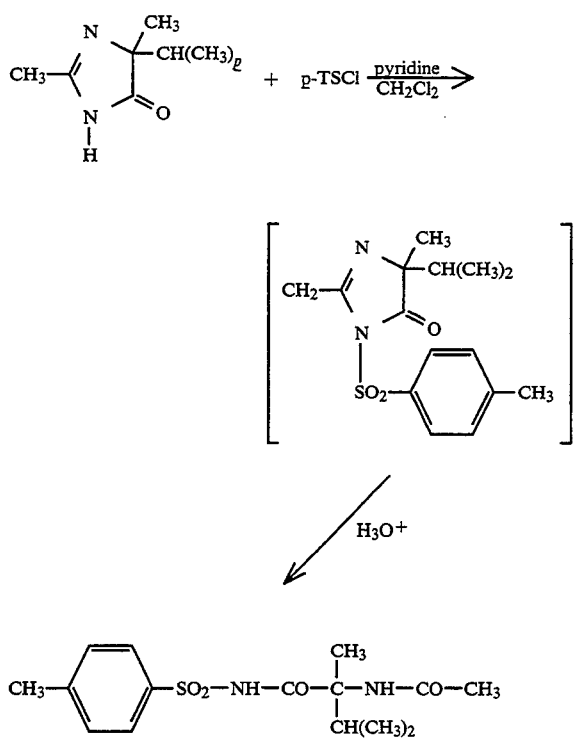

p-Toluenesulfonyl chloride (2.4 g, 12.97 mmol) is added to a stirred solution of 2,4-dimethyl-4-isopropyl-1,3-imidazolin-5-one in 40 mL of methylene chloride and 1.44 g of pyridine, cooled to −10° C. under N₂. Then the reaction mixture is allowed to warm to room temperature and stir for 16 hours.

The reaction mixture is checked for completeness of formation of 4-isopropyl-2,4-dimethyl-1-(p-tolylsulfonyl)-2-imidazolin-5-one by infrared spectroscopy. The product imidazolin-5-one is then hydrolyzed by diluting the solution with 100 mL of methylene chloride and washing twice with water and once with HCl 10%. The organic layer is concentrated in vacuo and the resulting yellowish oily residue is shaken with ether and allowed to stand. Upon standing the title product precipitates as a white solid, which after filtration, washing and drying has a mp of 202°–203° C.

Utilizing the above procedure with the appropriate sulfonyl chloride and starting imidazolinone yields the formula I herbicidal 2-imidazolin-5-one intermediates and herbicidal formula II compounds listed in Table II below.

TABLE II

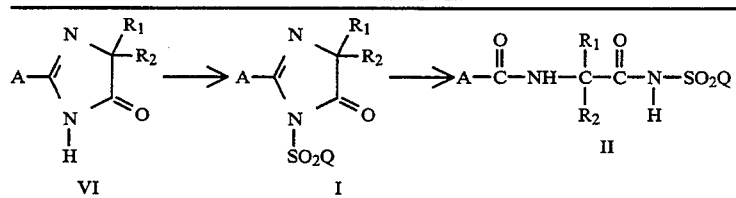

| Formula VI | | | Formula I | Means of | Formula II Compound | Formula II |
|---|---|---|---|---|---|---|
| A | $R_1$ | $R_2$ | Q | Identification | mp °C. | Example |
| $CH_3$ | $CH_3$ | i-$C_3H_7$ | p-tolyl | IR | 202–203 | $6a_1$ |
| H | $CH_3$ | i-$C_3H_7$ | 2-chlorophenyl | IR | 186–187 | $6b_1$ |
| H | $CH_3$ | i-$C_3H_7$ | 4-chlorophenyl | IR | 142–145 | $6c_1$ |
| H | $CH_3$ | i-$C_3H_7$ | p-tolyl | IR | 131–135 sint gum | $6d_1$ |
| $CH_3$ | $CH_3$ | i-$C_3H_7$ | o-carbomethoxy | IR | 157–160 | $6e_1$ |
| $CH_3$ | $CH_3$ | i-$C_3H_7$ | 4-methoxyphenyl | IR | 176–179 | $6f_1$ |
| $CH_3$ | $CH_3$ | i-$C_3H_7$ | 2-nitrophenyl | IR | 204–206 | $6g_1$ |
| $CH_3$ | $CH_3$ | i-$C_3H_7$ | 2-chlorophenyl | IR | 192–194 | $6h_1$ |
| $CH_3$ | $CH_3$ | i-$C_3H_7$ | phenyl | IR | 170–172 | $6i_1$ |
| $CH_3$ | $CH_3$ | i-$C_3H_7$ | 4-chlorophenyl | IR | 187–188 | $6j_1$ |
| $CH_3$ | $CH_3$ | i-$C_3H_7$ | 4-nitrophenyl | IR | 211–213 | $6k_1$ |
| $CH_3$ | $CH_3$ | i-$C_3H_7$ | 4-chloro-3-nitrophenyl | IR | 209–210 | $6l_1$ |
| $CH_3$ | $CH_3$ | i-$C_3H_7$ | 4-fluorophenyl | IR | 183–184 | $6m_1$ |
| $CH_3$ | $CH_3$ | i-$C_3H_7$ | p-tolyl | IR | 201–203 S $[\alpha]_D^{25} = +36.62$ | $6n_1$ |
| $CH_3$ | $CH_3$ | i-$C_3H_7$ | 3-nitrophenyl | IR | 196–198 | $6o_1$ |
| $CH_3$ | $CH_3$ | i-$C_3H_7$ | 4-chlorophenyl | IR | 202–203 R $[\alpha]_D^{25} = -25.98$ | $6p_1$ |
| $CH_3$ | $CH_3$ | i-$C_3H_7$ | o-tolyl | IR | 195–199 | $6q_1$ |
| $CH_3$ | $CH_3$ | i-$C_3H_7$ | 3,4-dichlorophenyl | IR | 204–206 | $6r_1$ |
| $CH_3$ | $CH_3$ | i-$C_3H_7$ | 2,5-dichlorophenyl | IR | 208–210 | $6s_1$ |
| $CH_3$ | $CH_3$ | i-$C_3H_7$ | 2,3,4-trichlorophenyl | IR | 222–223 | $6t_1$ |
| $CH_3$ | $CH_3$ | i-$C_3H_7$ | 2,4,5-trichlorophenyl | IR | 206–207 | $6u_1$ |
| $CH_3$ | $CH_3$ | i-$C_3H_7$ | 4-t-butylphenyl | IR | 167–171 | $6v_1$ |
| $CH_3$ | $CH_3$ | i-$C_3H_7$ | 2,4-xylyl | IR | 212–214 | $6w_1$ |
| $CH_3$ | $CH_3$ | i-$C_3H_7$ | 2,3,5,6-tetramethylphenyl | IR | 185–187 | $6x_1$ |
| $CH_3$ | $CH_3$ | i-$C_3H_7$ | 4-iodophenyl | IR | 185–187 | $6y_1$ |
| $CH_3$ | $CH_3$ | i-$C_3H_7$ | 4-acetamidophenyl | IR | 218–222 | $6z_1$ |
| $CH_3$ | $CH_3$ | i-$C_3H_7$ | (mesityl) 2,4,6-trimethylphenyl | IR | 192–194 | $6a_2$ |
| $CH_3$ | $CH_3$ | i-$C_3H_7$ | 2,4-dinitrophenyl | IR | 158–160 | $6b_2$ |
| $CH_3$ | $CH_3$ | i-$C_3H_7$ | 4-bromophenyl | IR | 190–193 | $6c_2$ |
| $CH_3$ | $CH_3$ | i-$C_3H_7$ | 2-naphthyl | IR | 165–170 | $6d_2$ |
| $CH_3$ | $CH_3$ | i-$C_3H_7$ | pentafluorophenyl | IR | 200–202 | $6e_2$ |
| $CH_3$ | $CH_3$ | i-$C_3H_7$ | 4-sec-butylphenyl | IR | 184–188 | $6f_2$ |
| $CH_3$ | $CH_3$ | i-$C_3H_7$ | 4-chloro-3-trifluoromethylphenyl | IR 2 | 192–195 | $6g_2$ |
| $CH_3$ | $CH_3$ | i-$C_3H_7$ | 2,5-xylyl | IR | 197–198 | $6h_2$ |
| $CH_3$ | $CH_3$ | i-$C_3H_7$ | 3-trifluoromethylphenyl | IR | 153–163 | $6i_2$ |
| $CH_3$ | $CH_3$ | i-$C_3H_7$ | 2-trifluoromethylphenyl | IR | 186–194 | $6j_2$ |
| $CH_3$ | $CH_3$ | i-$C_3H_7$ | 4-chlorophenyl | IR | 197–200 S+ $[\ ]_D^{25} = +24.91$ | $6k_2$ |
| $CH_3$ | $CH_3$ | i-$C_3H_7$ | 4-trifluoromethylphenyl | IR | 186–190 | $6l_2$ |
| $CH_3$ | $CH_3$ | i-$C_3H_7$ | 4-ethylphenyl | IR | 186–189 | $6m_2$ |
| $CH_3$ | $CH_3$ | i-$C_3H_7$ | 4-chloro-o-tolyl | IR | 215–216 | $6n_2$ |
| $CH_3$ | $CH_3$ | i-$C_3H_7$ | 4-cyanophenyl | IR | 209–212 | $6o_2$ |
| $CH_3$ | $CH_3$ | i-$C_3H_7$ | 4-carboxymethoxyphenyl | IR | 159–160 | $6p_2$ |
| $CH_3$ | $CH_3$ | i-$C_3H_7$ | 4-biphenyl | IR | 170–174 | $6q_2$ |
| $CH_3$ | $CH_3$ | i-$C_3H_7$ | 4-trifluoromethoxyphenyl | IR | 156–166 | $6r_2$ |
| $CH_3$ | $CH_3$ | i-$C_3H_7$ | 2-carboxyphenyl | IR | 179–180 | $6s_2$ |
| $CH_3$ | $CH_3$ | i-$C_3H_7$ | 2,4-dichlorophenyl | IR | 214–216 | $6t_2$ |
| $CH_3$ | $CH_3$ | i-$C_3H_7$ | 1-naphthyl | IR | 192–196 | $6u_2$ |
| $CH_3$ | $CH_3$ | i-$C_3H_7$ | m-tolyl | IR | 194–199 | $6v_2$ |
| $CH_3$ | $CH_3$ | i-$C_3H_7$ | 3-chlorophenyl | IR | 160–164 | $6w_2$ |
| $CH_3$ | $CH_3$ | i-$C_3H_7$ | 2,4-difluorophenyl | IR | 190–193 | $6x_2$ |

TABLE II-continued

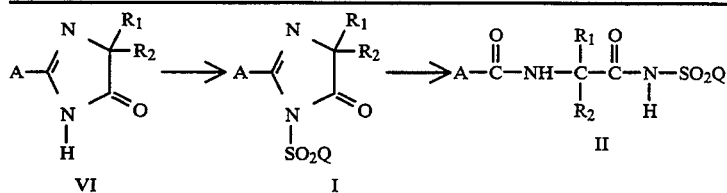

| Formula VI | | | Formula I | | Formula II | |
|---|---|---|---|---|---|---|
| A | $R_1$ | $R_2$ | Q | Means of Identification | Compound mp °C. | Formula II Example |
| $CH_3$ | $CH_3$ | $i$-$C_3H_7$ | 4-fluoro-3,5-xylyl | IR | 180–185 | $6y_2$ |
| $CH_3$ | $CH_3$ | $i$-$C_3H_7$ | 3,5-dichlorophenyl | IR | 190–195 | $6z_2$ |
| $CH_3$ | $CH_3$ | $i$-$C_3H_7$ | 4-acetoxyphenyl | IR | 175–180 | $6a_3$ |
| $CH_3$ | $CH_3$ | $i$-$C_3H_7$ | 4-chloro-2-trifluoromethylphenyl | IR | 206–208 | $6b_3$ |
| $CH_3$ | $CH_3$ | $i$-$C_3H_7$ | 2,4-dibromophenyl | IR | 208–210 | $6c_3$ |
| $CH_3$ | $CH_3$ | $i$-$C_3H_7$ | 4-chloro-2-cyanophenyl | IR | 184–186 | $6d_3$ |
| $CH_3$ | $CH_3$ | $i$-$C_3H_7$ | 3,5-dichloro-2-hydroxyphenyl | IR | 169–171 | $6e_3$ |
| $CH_3$ | $CH_3$ | $i$-$C_3H_7$ | 4,6-dichloro-$\underline{m}$-tolyl | IR | 225–226 | $6f_3$ |
| $CH_3$ | $CH_3$ | $i$-$C_3H_7$ | 4-aminophenyl monohydrate | IR | 204–206 | $6g_3$ |
| $CH_3$ | $CH_3$ | $i$-$C_3H_7$ | 3-chloro-4-fluorophenyl | IR | 196–202 | $6h_3$ |
| $CH_3$ | $CH_3$ | $i$-$C_3H_7$ | 4-vinylphenyl | IR | 165–172 | $6i_3$ |
| $CH_3$ | $CH_3$ | $i$-$C_3H_7$ | 5-bromo-2-methoxyphenyl | IR | 208–211 | $6j_3$ |
| $CH_3$ | $CH_3$ | $i$-$C_3H_7$ | 4-acetylphenyl | IR | 179–183 | $6k_3$ |
| $OCH_3$ | $CH_3$ | $i$-$C_3H_7$ | 4-chlorophenyl | IR | 134–135 | $6l_3$ |
| $CH_3$ | $CH_3$ | $i$-$C_3H_7$ | 4-fluoro-$\underline{o}$-tolyl | IR | 206–210 | $6m_3$ |
| $CH_3$ | $CH_3$ | $i$-$C_3H_7$ | 2-chloro-$\underline{p}$-tolyl | IR | 210–213 | $6n_3$ |
| $CH_3$ | $CH_3$ | $i$-$C_3H_7$ | 3-bromophenyl | IR | 200–202 | $6o_3$ |
| $CH_3$ | $CH_3$ | $i$-$C_3H_7$ | 6-chloro-$\underline{o}$-tolyl | IR | 222–225 | $6p_3$ |
| $CH_3$ | $C_2H_5$ | $C_2H_5$ | $p$-tolyl | IR | 180–181 | $6q_3$ |
| $CH_3$ | $CH_3$ | $C_2H_5$ | $p$-tolyl | IR | 170–174 | $6r_3$ |
| $CH_3$ | $C_2H_5$ | $i$-$C_3H_7$ | $p$-tolyl | IR | 145–147 | $6s_3$ |
| $CH_3$ | $CH_3$ | cyclopropyl | $p$-tolyl | IR | 187–188 | $6t_3$ |
| $CH_3$ | $CH_3$ | $i$-$C_3H_7$ | 2,6-dichlorophenyl | IR | 219–220 | $6u_3$ |
| $CH_3$ | $CH_3$ | $i$-$C_3H_7$ | 4-bromo-2,5-difluorophenyl | IR | 229–222 | $6v_3$ |
| $CH_3$ | $CH_3$ | $i$-$C_3H_7$ | 2-chloro-5-trifluoromethylphenyl | IR | 195–198 | $6w_3$ |
| $CH_3$ | $CH_3$ | $i$-$C_3H_7$ | 2,5-dibromo-3,6-difluorophenyl | IR | 197–198 | $6x_3$ |

EXAMPLE 7

Preparation of 2-formamido-2,3-dimethyl-N-(p-tolylsulfonyl)butyramide

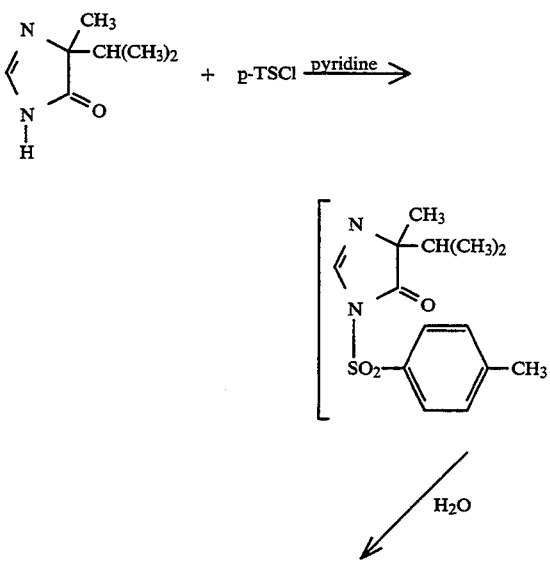

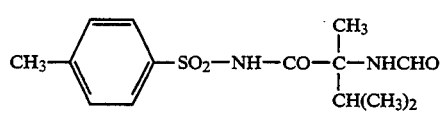

p-Toluenesulfonyl chloride (153.42 g, 0.0815 mol) is added to a stirred solution of 4-methyl-4-isopropyl-1,3-imidazolin-5-one, (112 g, 0.815 mol) in 1200 mL of methylene chloride, cooled to $-12°$ C. under a nitrogen atmosphere. Pyridine (91 mL) is then added, and the reaction mixture is allowed to stir at -10° C. for three hours and then allowed to attain room temperature. The completeness of formation of the intermediate imidazolinone is determined by IR. The intermediate imidazolinone is hydrolyzed by washing the reaction mixture once with 500 mL of aqueous HCl 10%, and once with water. The two-layer mixture is allowed to stand for 30 minutes and the resulting white solid filtered off and washed with ether, to yield 217.65 g of the title product as a white solid having mp 131°–135° C.

Substitution of p-chlorobenzenesulfonyl chloride for p-toluenesulfonyl chloride above affords 2-formamido-2,3-dimethyl-N-(p-chlorobenzenesulfonyl)butyramide, mp 142°–145° C.

EXAMPLE 8

Preparation of 2-amino-2,3-dimethyl-N-(p-tolylsulfonyl)butyramide hydrochloride

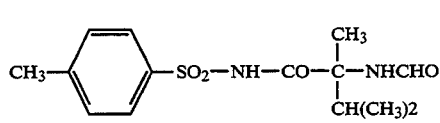

↓ HCl/H₂O/MeOH

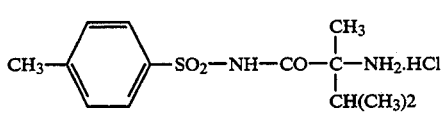

A suspension of 2-formamido-2,3-dimethyl-N-(p-tolylsulfonyl)butyramide (99.4 g, 0.318 mols) in 500 mL of methanol, 500 mL of water, and 500 mL of aqueous HCl 10% is heated at 80° C. until all the solid has dissolved (one hour). The reaction mixture is concentrated to ⅓ of the volume and the resulting precipitate is filtered off. After drying the title product is obtained as a white solid, having mp 161°-165° C.

Substitution of 2-formamido-2,3-dimethyl-N-(p-chlorobenzenesulfonyl)butyramide, affords 2-amino-2,3-dimethyl-N-(p-chlorobenzenesulfonyl)butyramide hydrochloride, mp 170°-172° C.

EXAMPLE 9

Preparation of 2-acetamido-2,3-dimethyl-N-(p-tolylsulfonyl)butyramide—Method B

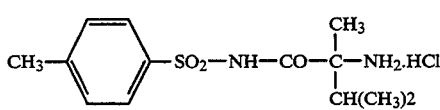

↓ Ac₂O pyridine

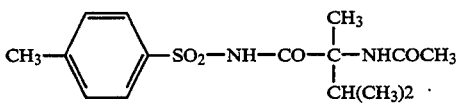

2-Amino-2,3-dimethyl-N-(p-tolylsulfonyl)butyramide hydrochloride (45 g ~0.4 mols) is completely dissolved in 160 mL of pyridine and 500 mL of THF is added. Acetic anhydride (45 mL) is then poured into the solution and the reaction mixture is heated at reflux for one hour. The solvents are removed under reduced pressure, and the oily residue is crystallized from EtOH/water affording 33.09 g of the title product having m.p. 198°-199° C.

EXAMPLE 10a

Preparation of 2,3-dimethyl-2-propionamido-N-(p-tolylsulfonyl)-butyramide

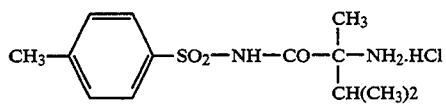

↓ CH₃—CH₂COCl  Et₃N, toluene

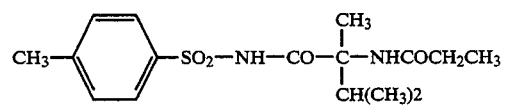

2-Amino-2,3-dimethyl-N-(p-tolylsulfonyl)butyramide hydrochloride (1.2 g, 5.3 mol) is dissolved in 25 mL of toluene under N₂. Then triethylamine (1.9 mL, 2.5 equivalents) is added, followed by immediate addition of propionyl chloride (0.55 mL, 6.36 mol). The reaction mixture is heated for one hour, and then solvents are removed under reduced pressure. The yellowish residue is recrystallized from EtOH/water, to yield the title product as a white solid having mp 166°-168° C.

Utilizing the above procedure with different acid chlorides yields the herbicidal formula II compounds listed in Table III below.

TABLE III $$R_5\text{—C}_6H_4\text{—SO}_2NH\text{—CO—C(CH}_3)(CH(CH_3)_2)\text{—NH—CO—A}$$

| Example | A | $R_5$ | mp °C. |
|---|---|---|---|
| 10b | $C_2H_5$ | $CH_3$ | 166–168 |
| c | $CH(CH_3)_2$ | $CH_3$ | 172–174 |
| d | $n\text{-}C_4H_9$ | $CH_3$ | 165–168 |
| e | $CH_2\text{—O—}CH_3$ | $CH_3$ | 165–167 |
| f | $CH_2CH(CH_3)_2$ | $CH_3$ | 174–176 |
| g | $C_3H_7$ | $CH_3$ | 188–190 |
| h | $CH_2CH=CH_2$ | $CH_3$ | 186–191 |
| i | $CH=CH\text{—}CH_3$ | $CH_3$ | 194–197 |
| j | $CH=CH\text{—}C_6H_5$ | $CH_3$ | 208–212 |
| k | $CH=CH_2$ | $CH_3$ | 180–182 |
| l | $CH_2COOCH_2CH_3$ | $CH_3$ | 162–165 |
| m | $C(=CH_2)CH_3$ | $CH_3$ | 139–149 |
| n | $CH=CH_2$ | Cl | 165–166 |
| o | $CH=CHCH_3$ | Cl | 177–180 |
| 10p | $CH_2O\text{—}C_6H_5$ | Cl | 164–167 |
| q | $CH_2CH_2Cl$ | $CH_3$ | — |
| r | $SCH_3$ | $CH_3$ | — |

TABLE III-continued

| Example | A | $R_5$ | mp °C. |
|---|---|---|---|
| s | $SOCH_3$ | $CH_3$ | — |
| t | $SO_2CH_3$ | $CH_3$ | — |
| u | phenyl | $CH_3$ | — |
| v | CH=CHCl | $CH_3$ | — |
| w | CCl=CHCl | $CH_3$ | — |
| x | $CHClCH_2Cl$ | $CH_3$ | — |
| y | $CH_3\overset{O}{\overset{\|}{C}}$ | $CH_3$ | — |
| z | $CF_3$ | $CH_3$ | — |

EXAMPLE 11a

Preparation of 1-{1,2-dimethyl-1-[(p-tolylsulfonyl)carbamoyl]propyl}-3-methylurea

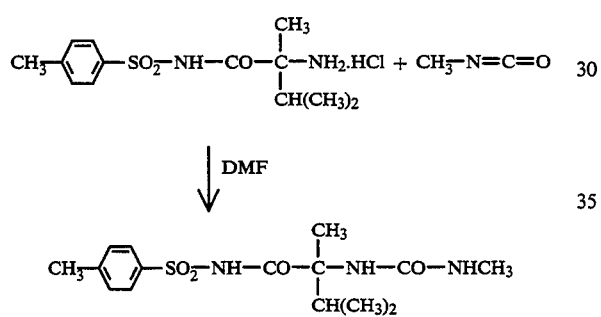

A solution of 2-amino-2,3-dimethyl-N-(p-tolylsulfonyl)butyramide hydrochloride (5 g, 15.58 mmols) dissolved in 50 mL of DMF under nitrogen is cooled to −30° C. Then 10 mL of methyl isocyanate in 10 mL of THF is added at such a rate that temperature is maintained at −30° C., and the reaction mixture is allowed to stir for two hours at −30° C. and then for 16 hours at room temperature.

The THF is removed by concentration in vacuo and water is added. The white solid which precipitates is filtered off and dried to yield the title product, 1.5 g, having mp 170°–171° C.

Utilizing the above procedure with different 1-sulfonylcarbamoylamines and isocyanates yields the formula II compounds listed in Table IV below.

TABLE IV $R_5$—C$_6$H$_4$—SO$_2$—NH—C(CH$_3$)(CH(CH$_3$)$_2$)—NH—CO—A

| Example | A | $R_5$ | mp °C. |
|---|---|---|---|
| 11b | $NHCH_2CH_2CH_2CH_3$ | $CH_3$ | 160–162 |
| c | $NHCH(CH_3)_2$ | $CH_3$ | 175–178 |
| d | NH-cyclohexyl | $CH_3$ | 172–174 |
| e | $NHCH_2CH_2Cl$ | $CH_3$ | 172–173 |
| f | $NHCH_2CH=CH_2$ | $CH_3$ | 167–169 |
| g | $NHCH_2CH_2CH_3$ | $CH_3$ | 163–165 |
| h | NH-phenyl | $CH_3$ | 210–212 |
| i | $NH-CH_2$-phenyl | $CH_3$ | 167–168 |
| j | $NHCH_3$ | Cl | 159–160 |

EXAMPLE 12

Preparation of the zwitterion of 2-amino-2,3-dimethyl-N-(p-tolylsulfonyl)butyramide

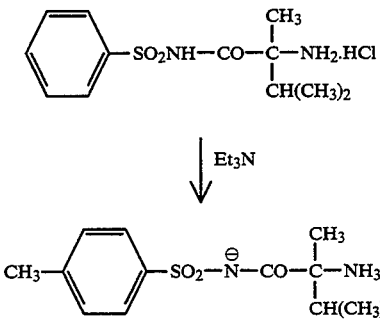

2-Amino-2,3-dimethyl-N-(p-tolylsulfonyl)butyramide hydrochloride (20 g, 62.34 mmol) is dissolved in 100 mL of water and 50 mL of ethanol. Triethylamine is then added until the pH of the reaction mixture is approximately 11, and the resulting solution is stirred for one hour.

The pH of the reaction mixture is adjusted to pH 6 with 10% aqueous HCl and the resulting white precipitate is filtered off, washed with water, and dried to yield the title compound as a white solid having mp 262°–265° C.

Utilizing the above procedure and substituting sodium bicarbonate for triethylamine also yields the desired zwitterion.

EXAMPLE 13

Preparation of
1-{1,2-dimethyl-[(p-tolylsulfonyl)carbamoyl]propyl}-3-methylurea

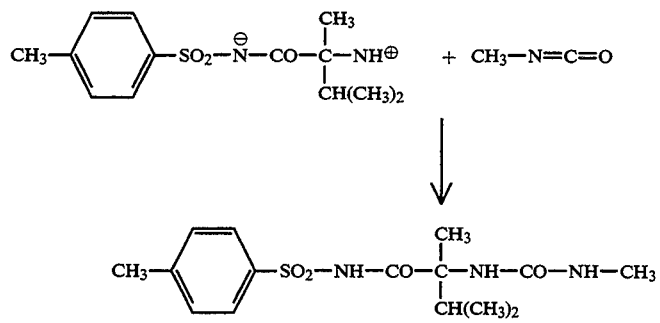

Methyl isocyanate (0.42 g, 4.22 mmol) is added to a stirred solution containing 1 g (3.52 mmoles) of the zwitterion of 2-amino-2,3-dimethyl-N-(p-tolylsulfonyl)-butyramide in 10 mL of dry DMF (dried over dessicant), under a nitrogen atmosphere, cooled at −20° C. in dry-ice/acetone bath. Then the temperature of the reaction mixture is allowed to attain room temperature and stir for one hour. Water (10 mL) is added and the product precipitates as a white solid, which is filtered off, washed with water, and dried, to afford 0.6 g of the title compound as a white solid which upon crystallization from DMF/water has mp 120°–125° C.

EXAMPLE 14

Preparation of
2-acetamido-2,3-dimethyl-N-)p-tolylsulfonyl)butyramide

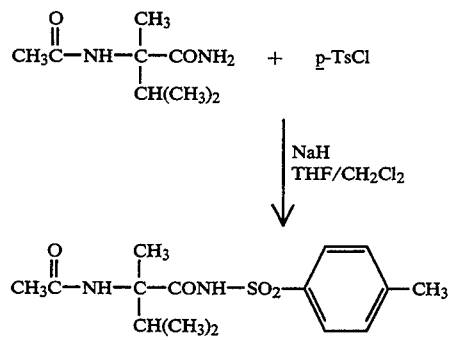

Sodium hydride (0.51 g, 60%) is added to a stirred solution of 2-N-acetyl-2,3-dimethylbutyramide (2 g, 11.6 mmols) in 40 mL of dry THF and 20 mL of dry methylene chloride under a nitrogen atmosphere, cooled to −20° C. with a dry-ice/acetone bath. When no more bubbles evolve, 2.21 g of p-toluenesulfonyl chloride is added and the temperature of the reaction mixture is allowed to attain room temperature and then stir for two hours, maintaining the temperature with a water bath (reaction is exothermic). Then 100 mL each of methylene chloride and aqueous sodium bicarbonate is added. The resulting aqueous solution is washed with methylene chloride, filtered, and the filtrate acidified to pH 2. The title compound precipitates as a white solid, which after filtration and drying affords 1.5 g as a white solid having mp 200°–204° C.

EXAMPLE 15

Preparation of
2,4-dimethyl-4-isopropyl-2-oxazolin-5-one

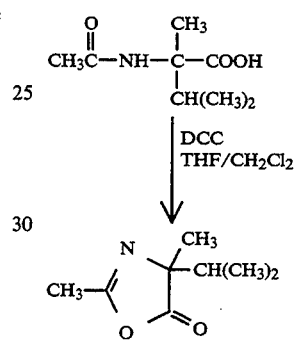

2-Acetamido-2,3-dimethylbutyric acid (16 g) is dissolved in THF (200 mL) and dicyclohexylcarbodiimide (DCC, 21.0 g) is added. The mixture is allowed to stir for 16 hours at 25° C. At the end of this time the mixture is filtered and evaporated to dryness. The residue is dissolved in $CH_2Cl_2$ (10 mL) and filtered again. Evaporation of the filtrate gives the crude product which is purified by distillation at 0.65 mmHg, having bp 50° C.

EXAMPLE 16

Preparation of
2-acetamido-2,3-dimethyl-N-(p-tolylsulfonyl)butyramide

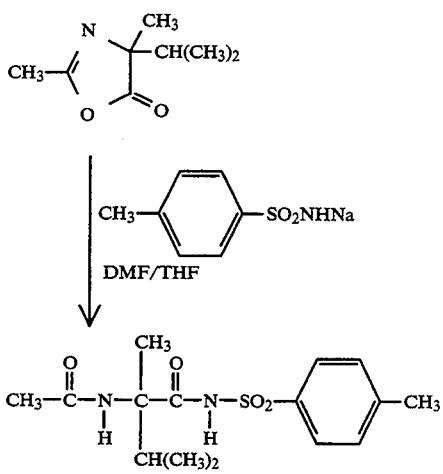

2,4-Dimethyl-4-isopropyl-2-oxazolin-5-one (2.0 g) is mixed with DMF (50 mL), THF (70 mL) and sodium p-toluene sulfonamide (5.0 g), and the resulting mixture is heated at reflux for 16 hours. At the end of this time the mixture is cooled, and the solvents are removed under vacuum. The residue is mixed with water and the pH adjusted to 8 with NaHCO3. The aqueous mixture is extracted with ethyl acetate and the organic layers are discarded. The aqueous mixture is acidified to pH24 with HCl and saturated with NaCl and extracted with ethyl acetate. The organic extracts are combined, dried over MgSO4, filtered and evaporated to give 0.66 of the title product.

EXAMPLE 16a

Preparation of 2-acetamido-2,3-dimethyl-N-(p-tolylsulfonyl)butyramide

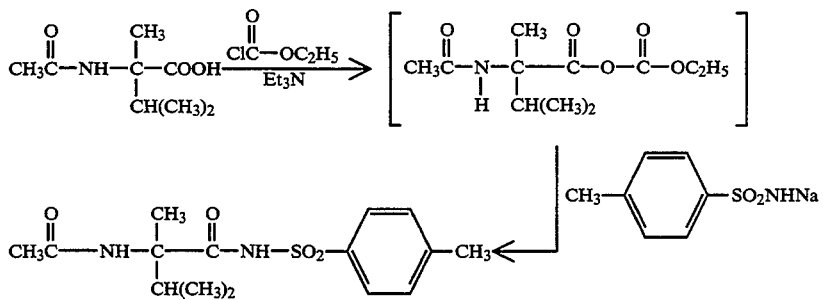

2-Acetamido-2,3-dimethylbutyric acid (1.5 g) is dissolved in a solution of triethylamine (2.7 g) in diethyl ether (50 mL) and cooled to 0° C.; ethylchloroformate (1.1 g) is added dropwise and the mixture is stirred at 0° to room temperature over one hour. The mixture is filtered, and the filtrate is concentrated in vacuo to afford the oily mixed anhydride (1.5 g). This material is mixed with 3 g of p-toluenesulfonamide, sodium salt, in 25 mL dimethylformamide, and the resulting mixture is heated at 80° C. for 16 hours. The reaction is cooled, concentrated in vacuo, and the residue is partitioned between methylene chloride and saturated, aqueous sodium bicarbonate. Acidification of the aqueous layer with conc. HCl to pH 1, extraction with CH2Cl2, drying, and stripping the organic phase affords the title product (3.3 g).

EXAMPLE 17

Preparation of 5-isopropyl-5-methyl-3-(p-tolylsulfonyl)hydantoin and 5-isopropyl-5-methyl, 1,3-bis(p-tolylsulfonyl)hydantoin

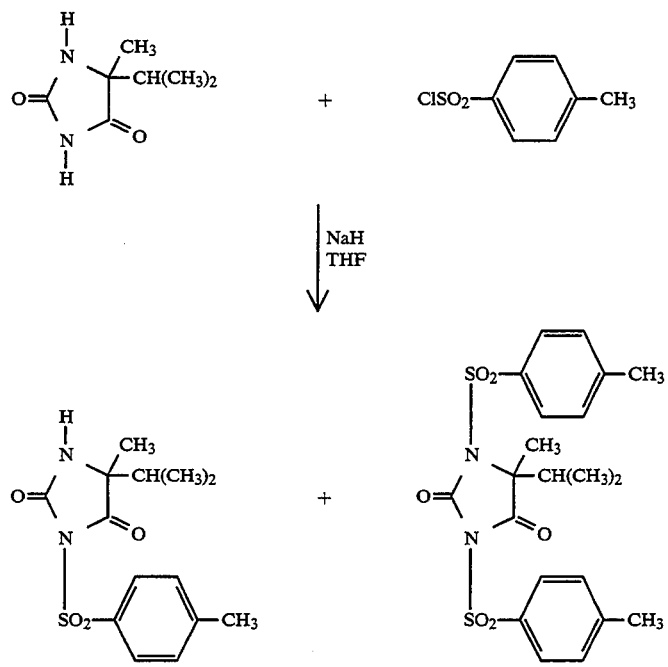

p-Toluenesulfonyl chloride (12.21 g) in 10 mL THF is added to a stirred mixture of 5-isopropyl-5-methyl hydantoin (10 g, 0.064 mol) and sodium hydride (2.56 g) in 90 mL THF and the reaction mixture is allowed to stir under a nitrogen atmosphere for 16 hours. The reaction mixture is filtered and the filtrate concentrated to a tan oil 14.2 g. A thin layer chromatograph of the mixture on silica gel with 10% CH3CN/CH2Cl2 eluant showed two products which are separated by column chromatography on silica gel with 10% CH3CN/CH2Cl2 as eluant to give Fraction 1, 5-isopropyl-5-methyl-1,3-bis(p-tolylsulfonyl)hydantoin (2.1 g) having mp 144°–146° C. and Fraction 2, 5-isopropyl-5-methyl-3-(p-tolylsulfonyl)-hydantoin (7.2 g) having mp 102°–103° C.

EXAMPLE 18

Preparation of methylamine salt of 1-{1{[p-chlorophenyl)sulfonyl]carbamoyl}-1,2-dimethylpropyl}-3-methylurea A mixture of 5-isopropyl-5-methyl-3-(p-chlorosulfonyl)hydantoin (2.0 g) and methylamine (10 mL, 40% aqueous solution) in tetrahydrofuran (THF, 50 mL) is allowed to stir at room temperature for 16 hours. The reaction mixture is concentrated under reduced pressure and the resulting residue dissolved in water and filtered. The filtrate is acidified to pH 3 and the resulting solid collected by filtration. The solid, 1.4 g, is dissolved in THF (50 mL) and methylamine (10 mL, 40%) is added. The mixture is stirred for one hour and then concentrated under reduced pressure to yield the title product (1.3 g) as a white solid having mp 120°–122° C.

By utilizing the above procedure and substituting the appropriately substituted hydantoin and methanol as reactants, methyl (1,2-dimethyl-1-[(p-tolylsulfonyl)carbamoyl]propyl}carbamate having mp 120°–122° C. is obtained, and by substituting 1,1-dimethylhydrazine for methylamine yields 4-(1,2-dimethyl-1-[(p-tolylsulfonyl)-carbamoyl]propyl)-1,1-dimethylsemicarbazide having m.p. 96°–98° C.

EXAMPLE 19

Preparation of isopropylamine salt of 2-acetamido-N-[4-chloro-o-tolyl)sulfonyl]-2,3-dimethylbutyramide

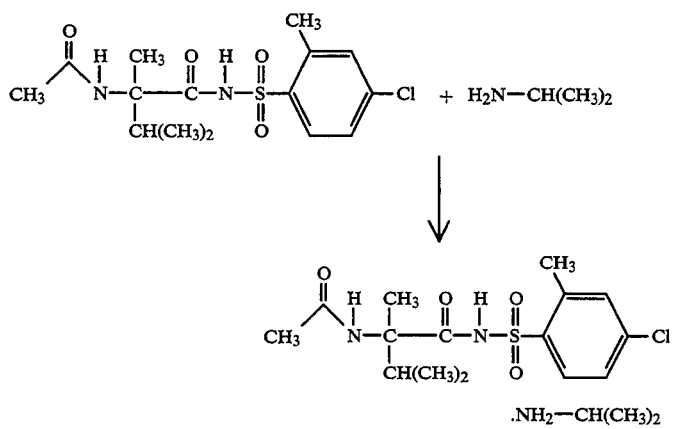

A solution of 1.0 g (2.8 mmols) of 2-acetamido-N-[(4-chloro-o-tolyl)sulfonyl]-2,3-dimethylbutyramide in 50 mL of THF at 25° C. is treated with 0.17 g (2.9 mmols) of isopropylamine. The resulting mixture is stirred at 25° C. for one hour, after which the solution is diluted with 50 mL diethyl ether. The resulting suspension is stirred for 15 minutes, and the solid which forms is collected by filtration. This solid is washed with two 50 mL portions of warm THF and air dried to afford 0.97 g (84%) of the title product as a beige solid having mp 161°–163° C.

EXAMPLE 20

Preparation of sodium salt of 2-acetamido-2,3-dimethyl-N-(p-tolylsulfonyl)butyramide

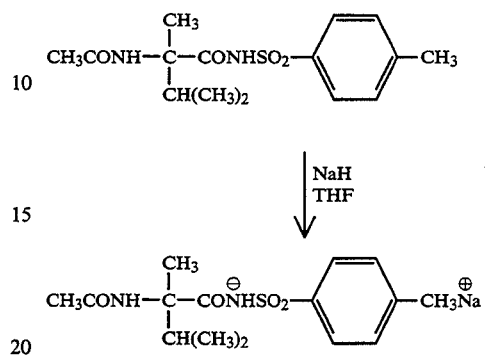

Solid NaH (0.24 g, of 50% NaH, 0.005 mols) is added all at once to a stirred solution of 2-acetamido-2,3-dimethyl-N-(p-tolylsulfonyl)butyramide (1.63 g, 0.005 mols) in 20 mL THF. Stirring is continued for one hour and the resulting white solid is filtered and dried to give the title product (1.36 g, 78.1%) having mp 167°–169° C.

EXAMPLE 21

Utilizing the above procedures described in examples 17–19 yields the salts listed in Table V below.

TABLE V $$\underset{\text{salt}}{\overset{\text{O} \quad\quad \text{CH}_3 \quad \text{O}}{\text{A}-\overset{\|}{\text{C}}-\text{NH}-\underset{\underset{\text{CH}(\text{CH}_3)_2}{|}}{\overset{|}{\text{C}}}-\overset{\|}{\text{C}}-\text{NHSO}_2\text{Q}}}$$

| Example | A | Q | Salt | mp °C. |
|---|---|---|---|---|
| 21a | CH₃ | p-tolyl | isopropylamine | 144–146 |
| 21b | CH₃ | 4-chlorophenyl | isopropylamine | 182–184 |
| 21c | CH₃ | 4,6-dichloro-m-tolyl | isopropylamine | 176–181 |
| 21d | CH₃ | 5-dimethylamino-1-naphthyl | isopropylamine | 88–128 |

EXAMPLE 22

Post-emergence herbicidal evaluation of test compounds

The postemergence herbicidal activity of the compounds of the present invention is demonstrated by the following tests, wherein a variety of monocotyledonous and dicotyledonous plants are treated with test compounds dispersed in aqueous acetone mixtures. In the tests, seedling plants are grown in jiffy flats for about two weeks. The test compounds are dispersed in 50 acetone/water mixtures containing 0.5% TWEEN 20, a polyoxyethylene sorbitan monolaurate surfactant of Atlas Chemical Industries, in sufficient quantity to provide the equivalent of about 0.032 kg to 8 kg per hectare of active compound when applied to the plants through a spray nozzle operating at 40 psi for a predetermined time. After spraying, the plants are placed on greenhouse benches and are cared for in the usual manner, commensurate with conventional greenhouse practices. From four to five weeks after treatment, the seedling plants, are examined and rated according to the rating system provided below. The data obtained are recorded in Table VI below.

| Rating system | % Difference in growth from the check* |
|---|---|
| 0 - No effect | 0 |
| 1 - Possible effect | 1–10 |
| 2 - Slight effect | 11–25 |
| 3 - Moderate effect | 26–40 |
| 5 - Definite injury | 41–60 |
| 6 - Herbicidal effect | 61–75 |
| 7 - Good herbicidal effect | 76–90 |
| 8 - Approaching complete kill | 91–99 |
| 9 - Complete kill | 100 |
| 4 - Abnormal growth, that is, a definite physiological malformation but with an over-all effect less than a 5 on the rating scale. | |

In most cases the data are for a single test, but in several instances, they are average values obtained from more than one test.

| Abbreviation | Plant Species Used Common Name | Scientific Name |
|---|---|---|
| BARNYARDGR | Barnyardgrass | Echinochloa crus-galli (L) Beau |
| FOXTAIL SP | Foxtail, Spp. | Setaria Spp. |
| P NUTSEDGE | Nutsedge, Purple | Cyperus rotundus, L. |
| WILD OATS | Oat, Wild | Avena fatua, L. |
| QUACKGRASS | Quackgrass | Agropyron repens, (L) Beauv. |
| FLD bindwd | Bindweed, Field (Rhizome) | Convolvulus arvensis, L. |
| MATRIC SPP | Matricaria Spp. | Matricaria Spp. |
| MRNGLRY SP | Morningglory Spp. | Ipomoea Spp. |
| WILD MUST | Mustard, Wild | Brassica kaber, (DC) L.C. Wheelr |
| RAGWEED | Ragweed, Common | Ambrosia artemisiifolia L. |
| VELVETLEAF | Velvetleaf | Abutilon theophrasti, medic. |

TABLE VI

POST-EMERGENCE TESTS - RATES IN KG/HA

| Compound of Example | RATE | BARNY ARDGR | FOXTA IL SP | P NUT SEDGE | WILD OATS | QUACK GRASS | FLD B INDWD | MATRI C SPP | MRNGL RY SP | WILD MUSTD | RAG WEED | VELVE TLEAF |
|---|---|---|---|---|---|---|---|---|---|---|---|---|
| 5a | 2.000 | | | 0.0 | | 0.0 | | 3.0 | 0.0 | 0.0 | 0.0 | 1.0 |
| | 1.500 | | | 0.0 | | 0.0 | | 2.0 | 0.0 | 0.0 | 0.0 | 4.0 |
| | 1.000 | 0.0 | 3.0 | 1.5 | 0.0 | 1.0 | 6.0 | 2.0 | 3.0 | 0.0 | 3.5 | 4.5 |
| | .750 | | | 0.0 | | 0.0 | | 1.0 | 0.0 | 0.0 | 0.0 | 0.0 |
| | .500 | 0.0 | 1.0 | 0.5 | 0.0 | 0.5 | 4.0 | 1.0 | 1.0 | 0.0 | 4.0 | 4.5 |
| 5b | 4.000 | 6.0 | 9.0 | 9.0 | 9.0 | 9.0 | 9.0 | | 9.0 | 9.0 | | 9.0 |
| | 2.000 | 6.0 | 9.0 | 9.0 | 9.0 | 9.0 | 9.0 | | 9.0 | 9.0 | | 9.0 |
| | 1.000 | 4.0 | 7.0 | 9.0 | 9.0 | 9.0 | 7.0 | | 9.0 | 9.0 | | 9.0 |
| | .500 | 2.0 | 7.0 | 4.0 | 6.0 | 8.0 | 6.0 | | 9.0 | 9.0 | | 9.0 |
| 5d | 4.000 | 0.0 | 0.0 | 0.0 | 0.0 | 0.0 | 1.0 | | 7.0 | 9.0 | 3.0 | 1.0 |
| | 2.000 | 0.0 | 0.0 | 0.0 | 0.0 | 0.0 | 0.0 | | 7.0 | 8.0 | 2.0 | 1.0 |
| | 1.000 | 0.0 | 0.0 | 0.0 | 0.0 | 0.0 | 0.0 | | 8.0 | 8.0 | 3.0 | 0.0 |
| | .500 | 0.0 | 0.0 | 0.0 | 0.0 | 0.0 | 0.0 | | 4.0 | 7.0 | 0.0 | 0.0 |
| 5e | 4.000 | 3.5 | 9.0 | 3.0 | 8.5 | 8.5 | 3.0 | | 7.5 | 8.5 | 8.5 | 6.0 |
| | 2.000 | 7.0 | 6.0 | 4.0 | 9.0 | 9.0 | 6.0 | | 9.0 | 9.0 | 8.0 | 9.0 |
| | 1.000 | 7.0 | 6.0 | 1.0 | 9.0 | 9.0 | 4.0 | | 7.0 | 9.0 | 9.0 | 9.0 |
| | .500 | 3.0 | 1.0 | 0.0 | 4.0 | 7.0 | 3.0 | | 7.0 | 9.0 | 8.0 | 7.0 |
| 5f | 4.000 | 1.0 | 1.0 | 4.0 | 1.0 | 2.0 | 8.0 | | 9.0 | 9.0 | 8.0 | 9.0 |
| | 2.000 | 0.0 | 0.0 | 3.0 | 0.0 | 1.0 | 6.0 | | 9.0 | 9.0 | 9.0 | 9.0 |
| | 1.000 | 0.0 | 0.0 | 1.0 | 0.0 | | 6.0 | | 9.0 | 7.0 | 8.0 | 9.0 |
| | .500 | 0.0 | 0.0 | 1.0 | 0.0 | 0.0 | 6.0 | | 9.0 | 9.0 | 6.0 | 9.0 |
| 5g | 4.000 | 0.0 | 0.0 | 3.0 | 0.0 | 2.0 | 4.0 | | 7.0 | 7.0 | 6.0 | 7.0 |
| | 2.000 | 0.0 | 0.0 | 0.0 | 0.0 | 0.0 | 2.0 | | 7.0 | 7.0 | 5.0 | 5.0 |
| | 1.000 | 0.0 | 0.0 | 0.0 | 0.0 | 0.0 | | | 3.0 | 5.0 | 4.0 | 3.0 |
| | .500 | 0.0 | 0.0 | 0.0 | 0.0 | 0.0 | 2.0 | | 3.0 | 3.0 | 0.0 | 1.0 |
| 5h | 1.000 | 0.0 | 0.0 | 4.0 | 0.0 | 0.0 | 8.0 | | 8.0 | 9.0 | 8.0 | 9.0 |
| | .500 | 0.0 | 0.0 | 0.0 | 0.0 | 0.0 | 6.0 | | 7.0 | 9.0 | 7.0 | 8.0 |
| 6a$_1$ | 4.000 | 2.8 | 3.5 | 5.5 | 1.6 | 3.5 | 7.3 | | 6.0 | 9.0 | 8.3 | 9.0 |
| | 2.000 | 1.7 | 2.8 | 3.0 | 0.8 | 2.7 | 5.9 | 8.3 | 4.8 | 8.1 | 6.8 | 8.4 |
| | 1.500 | | | 0.0 | | 0.0 | | 5.0 | 0.0 | 0.0 | 0.0 | 1.0 |
| | 1.000 | 0.6 | 2.3 | 2.3 | 0.4 | 1.1 | 5.3 | 7.3 | 3.5 | 8.0 | 6.3 | 8.0 |
| | .750 | | | 0.0 | | 1.7 | | 6.0 | 2.5 | 5.3 | 0.0 | 4.5 |
| | .500 | 0.1 | 1.3 | 1.3 | 0.2 | 0.4 | 4.4 | 6.6 | 2.1 | 7.8 | 5.6 | 7.8 |
| 6b$_1$ | 1.000 | 0.0 | 0.0 | 0.0 | 0.0 | 0.0 | 3.0 | | 2.0 | | 2.0 | 1.5 |
| | .500 | 0.0 | 0.0 | 0.0 | 0.0 | 0.0 | 3.0 | | 1.0 | | 1.0 | 0.5 |

TABLE VI-continued
POST-EMERGENCE TESTS - RATES IN KG/HA

| | | | | | | | | | | | | |
|---|---|---|---|---|---|---|---|---|---|---|---|---|
| 6c₁ | 1.000 | 0.0 | 0.5 | 0.0 | 0.0 | 0.0 | 8.5 | | 2.0 | | 7.0 | 6.0 |
| | .500 | 0.0 | 0.0 | 0.0 | 0.0 | 0.0 | 7.5 | | 1.5 | | 5.5 | 4.5 |
| 6d₁ | 4.000 | 0.0 | | 0.0 | 1.0 | 0.0 | 9.0 | | 2.0 | 1.0 | 5.0 | 4.0 |
| | 1.000 | 0.0 | 0.0 | 0.0 | 0.0 | 0.0 | 7.0 | | 1.0 | | 6.0 | 4.0 |
| | .500 | 0.0 | 0.0 | 0.0 | 0.0 | 0.0 | | | 1.0 | | 7.0 | 4.0 |
| 6e₁ | 1.000 | 0.0 | 0.0 | 0.0 | 0.0 | 0.5 | 4.5 | | 4.0 | | 2.0 | 3.0 |
| | .500 | 0.0 | 0.0 | 0.0 | 0.0 | 0.0 | 4.0 | | 1.5 | | 1.0 | 2.0 |
| 6g₁ | 4.000 | 0.0 | 0.0 | 0.0 | 0.0 | 0.0 | 1.0 | | 1.5 | | 1.5 | 2.5 |
| | 2.000 | 0.0 | 0.0 | 0.0 | 0.0 | 0.0 | 0.0 | | 0.5 | | 2.0 | 0.0 |
| | 1.000 | 0.0 | 0.0 | 0.0 | 0.0 | 0.0 | 0.0 | | 0.5 | | 1.5 | 0.5 |
| | .500 | 0.0 | 0.0 | 0.0 | 0.0 | 0.0 | 0.0 | | 0.5 | | 1.5 | 0.0 |
| 6h₁ | 4.000 | 3.0 | 6.0 | 0.0 | 5.0 | 4.0 | 9.0 | | 8.0 | | 9.0 | 9.0 |
| | 2.000 | 3.0 | 5.0 | 0.0 | 5.0 | 2.0 | 9.0 | | 8.0 | | 9.0 | 9.0 |
| | 1.000 | 2.0 | 2.0 | 0.0 | 2.0 | 2.0 | 8.0 | | 7.0 | | 8.0 | 9.0 |
| | .500 | 0.0 | 1.0 | 0.0 | 2.0 | 1.0 | 7.0 | | 7.0 | | 8.0 | 7.0 |
| 6i₁ | 4.000 | 6.0 | 9.0 | 0.0 | 9.0 | 7.0 | 4.0 | | 6.0 | | 4.0 | 9.0 |
| | 2.000 | 3.0 | 9.0 | 0.0 | 5.0 | 6.0 | 4.0 | | 3.0 | | 2.0 | 9.0 |
| | 1.000 | 3.0 | 7.0 | 0.0 | 1.0 | 5.0 | 1.0 | | 2.0 | | 2.0 | 9.0 |
| | .500 | 1.0 | 4.0 | 0.0 | 0.0 | 5.0 | 0.0 | | 1.0 | | 2.0 | 9.0 |
| 6j₁ | 4.000 | 7.3 | 7.8 | 7.2 | 8.8 | 7.8 | 8.2 | | 8.0 | 9.0 | 8.8 | 9.0 |
| | 3.000 | 8.0 | 8.0 | 7.0 | 9.0 | 9.0 | 6.0 | | 7.0 | 9.0 | 9.0 | 9.0 |
| | 2.000 | 6.2 | 7.6 | 6.8 | 8.2 | 7.5 | 8.6 | 9.0 | 7.9 | 9.0 | 8.6 | 9.0 |
| | 1.000 | 3.7 | 5.0 | 5.9 | 7.7 | 7.5 | 7.5 | 9.0 | 7.8 | 9.0 | 8.5 | 8.8 |
| | .800 | 1.0 | 5.0 | 6.0 | 9.0 | 5.0 | 5.0 | | 7.0 | 9.0 | | 9.0 |
| | .750 | | | 0.0 | | 7.0 | | | 8.0 | 9.0 | 8.0 | 9.0 |
| | .500 | 2.4 | 5.1 | 2.9 | 6.1 | 5.9 | 5.5 | 9.0 | 6.9 | 9.0 | 7.4 | 8.6 |
| 6k₁ | 4.000 | 0.0 | 0.0 | 0.0 | 0.0 | 0.0 | 1.0 | | 0.0 | 8.0 | 6.0 | 4.0 |
| | .500 | 0.0 | 0.0 | 0.0 | 0.0 | 0.0 | 0.0 | | 0.0 | 7.0 | 5.0 | 1.0 |
| 6l₁ | 4.000 | 0.0 | 0.0 | 0.0 | 0.0 | 0.0 | 0.0 | | 0.0 | 5.0 | | 2.0 |
| | .500 | 0.0 | 0.0 | 0.0 | 0.0 | 0.0 | 0.0 | | 0.0 | 4.0 | 4.0 | 1.0 |
| 6m₁ | 4.000 | 9.0 | 9.0 | 8.0 | 6.0 | 6.0 | 9.0 | | 9.0 | 9.0 | 8.0 | 9.0 |
| | 2.000 | 9.7 | 9.0 | 8.0 | 9.0 | 9.0 | 6.0 | | 9.0 | 9.0 | 7.0 | 9.0 |
| | 1.000 | 6.7 | 9.0 | 2.7 | 8.5 | 8.0 | 7.0 | | 7.0 | 9.0 | 8.0 | 9.0 |
| | .500 | 4.8 | 6.7 | 1.3 | 8.0 | 6.3 | 5.3 | | 6.8 | 9.0 | 6.0 | 9.0 |
| 6n₁ | 4.000 | 8.0 | 6.0 | 9.0 | 2.0 | 7.0 | 9.0 | | 9.0 | 9.0 | | 9.0 |
| | 3.000 | 6.0 | 6.0 | 7.0 | 2.0 | 7.0 | 8.0 | | 8.0 | 9.0 | | 9.0 |
| | 2.000 | 1.0 | 4.0 | 7.0 | 1.0 | 6.0 | 6.0 | | 7.0 | 9.0 | | 9.0 |
| | 1.000 | 0.0 | 3.0 | 6.0 | 0.0 | 6.0 | 4.0 | | 6.0 | 9.0 | | 9.0 |
| | .800 | 0.0 | 2.0 | 4.0 | 0.0 | 5.0 | 4.0 | | 2.0 | 9.0 | | 9.0 |
| | .500 | 0.0 | 1.0 | 2.0 | 0.0 | | 4.0 | | 1.0 | 9.0 | | 9.0 |
| 6o₁ | 4.000 | 0.0 | 0.0 | 0.0 | 0.0 | 2.0 | 2.0 | | 6.0 | 9.0 | 7.0 | 4.0 |
| | .500 | 0.0 | 0.0 | 0.0 | 0.0 | 0.0 | 1.0 | | 0.0 | 3.0 | 0.0 | 1.0 |
| 6q₁ | 4.000 | 0.0 | 0.0 | 2.0 | 0.0 | 0.0 | 6.0 | | 8.0 | 9.0 | 8.5 | 9.0 |
| | 2.000 | 0.0 | 0.0 | 0.0 | 0.0 | 0.0 | 6.0 | | 8.0 | 9.0 | 7.0 | 9.0 |
| | 1.000 | 0.0 | 0.0 | 0.0 | 0.0 | 0.0 | 4.0 | | 2.0 | 9.0 | 7.0 | 7.0 |
| | .500 | 0.0 | 0.0 | 0.0 | 0.0 | 0.0 | 3.0 | | 4.7 | 9.0 | 6.0 | 7.0 |
| 6r₁ | 4.000 | 6.0 | 7.0 | 6.0 | 9.0 | 5.0 | 6.0 | | 8.0 | 9.0 | 9.0 | 9.0 |
| | 1.000 | 3.0 | 2.0 | 2.0 | 2.0 | 1.0 | 3.0 | | 4.0 | 9.0 | 8.0 | 8.0 |
| | .500 | 0.5 | 0.0 | 0.5 | 0.5 | 1.5 | 2.5 | | 2.5 | 9.0 | 7.5 | 6.0 |
| 6s₁ | 4.000 | 7.0 | 8.0 | 6.0 | 8.0 | 7.0 | 6.0 | | 8.0 | 9.0 | 8.0 | 9.0 |
| | 1.000 | 7.0 | 1.0 | 0.0 | 0.0 | 3.0 | 3.0 | | 8.0 | 9.0 | 7.0 | 8.0 |
| | .500 | 4.0 | 1.0 | 0.0 | 0.0 | 1.5 | 4.5 | | 7.0 | 9.0 | 7.0 | 7.5 |
| 6t₁ | 4.000 | 6.5 | 4.5 | 4.5 | 7.0 | 5.5 | 6.5 | | 8.0 | 9.0 | 7.0 | 7.0 |
| | 2.000 | 3.0 | 2.0 | 0.0 | 3.0 | 5.0 | 5.0 | | 7.0 | 9.0 | 7.0 | 7.0 |
| | 1.000 | 0.0 | 1.0 | 0.0 | 2.0 | 4.0 | 5.0 | | 7.0 | 9.0 | 7.0 | 2.0 |
| | .500 | 0.0 | 0.0 | 0.0 | 0.5 | 1.0 | 4.0 | | 5.7 | 8.5 | 7.0 | 2.5 |
| 6u₁ | 4.000 | 0.0 | 0.0 | 3.0 | 0.0 | 0.0 | 8.0 | | 8.0 | 9.0 | 8.0 | 9.0 |
| | 1.000 | 0.0 | 0.0 | 0.0 | 0.0 | 0.0 | 2.0 | | 2.5 | 9.0 | 5.0 | 1.0 |
| | .500 | 0.0 | 0.0 | 0.0 | 0.0 | 0.0 | 3.5 | | 3.3 | 8.5 | 6.5 | 3.5 |
| 6v₁ | 4.000 | 0.0 | 0.0 | | 0.0 | 0.0 | 1.0 | | 0.0 | 1.0 | 2.0 | 1.0 |
| | .500 | 0.0 | 0.0 | 0.0 | 0.0 | 0.0 | 0.0 | | 0.0 | 1.0 | 1.0 | 1.0 |
| 6w₁ | 4.000 | 0.0 | 1.5 | 3.5 | 0.0 | 0.5 | 9.0 | | 8.0 | 9.0 | 6.0 | 9.0 |
| | 2.000 | 0.0 | 0.0 | 2.0 | 0.0 | 0.0 | 9.0 | | 9.0 | 9.0 | 5.0 | 9.0 |
| | 1.000 | 0.0 | 0.0 | 0.0 | 0.0 | 0.0 | 6.0 | | 7.0 | 9.0 | 5.0 | 9.0 |
| | .500 | 0.0 | 0.0 | 0.0 | 0.0 | 0.0 | 5.5 | | 5.5 | 7.5 | 4.5 | 7.0 |
| 6x₁ | 4.000 | 0.0 | 0.0 | 2.0 | 0.0 | 0.0 | 0.0 | | 6.0 | 7.0 | | 5.0 |
| | .500 | 0.0 | 0.0 | 0.0 | 0.0 | 0.0 | 0.0 | | 3.0 | 4.0 | 0.0 | 2.0 |
| 6y₁ | 4.000 | 6.0 | 6.0 | 4.0 | 6.0 | 2.0 | 5.0 | | 6.0 | 9.0 | 9.0 | 9.0 |
| | .500 | 0.0 | 0.0 | 0.0 | 0.0 | 0.0 | 2.0 | | 2.0 | 9.0 | | 7.0 |
| 6z₁ | 4.000 | 0.0 | 0.0 | 0.0 | 0.0 | 0.0 | 0.0 | | 1.0 | 0.5 | 0.5 | 0.5 |
| | 2.000 | 0.0 | 0.0 | 0.0 | 0.0 | 0.0 | 0.0 | | 0.0 | 0.0 | 0.0 | 0.0 |
| | 1.000 | 0.0 | 0.0 | 0.0 | 0.0 | 0.0 | 0.0 | | 0.0 | 0.0 | 0.0 | 0.0 |
| | .500 | 0.0 | 0.0 | 0.0 | 0.0 | 0.0 | 0.0 | | 0.5 | 0.5 | 0.0 | 0.5 |
| 6a₂ | 4.000 | 0.0 | 0.0 | 5.0 | 0.0 | 0.0 | 9.0 | | 8.0 | 8.0 | 0.0 | 7.0 |
| | .500 | 0.0 | 0.0 | 0.0 | 0.0 | 0.0 | 4.0 | | 6.0 | 5.0 | | 4.0 |
| 6b₂ | 4.000 | 0.0 | 0.0 | 0.0 | 0.0 | 0.0 | 0.0 | | 0.0 | 0.0 | | |
| 6c₂ | 4.000 | 7.0 | 8.0 | 7.0 | 9.0 | 8.0 | 7.0 | | 9.0 | 9.0 | 9.0 | 9.0 |
| | 1.000 | 3.0 | 5.0 | 0.0 | 2.0 | 2.0 | 3.0 | | 5.0 | 9.0 | 8.0 | 8.0 |
| | .500 | 1.5 | 3.5 | 1.5 | 3.0 | 1.0 | 3.5 | | 5.5 | 9.0 | 8.0 | 8.0 |
| 6d₂ | 4.000 | 0.0 | 0.0 | 0.0 | 0.0 | 0.0 | 0.0 | | 0.0 | 5.0 | | 1.0 |
| | .500 | 0.0 | 0.0 | 0.0 | 0.0 | 0.0 | 0.0 | | 4.0 | 5.0 | | 1.0 |

TABLE VI-continued

POST-EMERGENCE TESTS - RATES IN KG/HA

| Cmpd | Rate | 1 | 2 | 3 | 4 | 5 | 6 | 7 | 8 | 9 | 10 | 11 |
|---|---|---|---|---|---|---|---|---|---|---|---|---|
| $6e_2$ | 4.000 | 1.0 | 0.0 | 1.0 | 1.0 | 0.0 | 1.0 | | 4.0 | 6.0 | 8.0 | 4.0 |
| | .500 | 0.0 | 0.0 | 0.0 | 0.0 | 0.0 | 1.0 | | 2.0 | 7.0 | 7.0 | 1.0 |
| $6f_2$ | 4.000 | 0.0 | 0.0 | 0.0 | 0.0 | 0.0 | 0.0 | | 0.0 | 0.0 | 2.0 | |
| | .500 | 0.0 | 0.0 | 0.0 | 0.0 | 0.0 | 0.0 | | 0.0 | 2.0 | 3.0 | 1.0 |
| $6g_2$ | 4.000 | 0.0 | 0.0 | 1.0 | 0.0 | 0.0 | 2.0 | | 2.0 | 7.0 | 6.0 | 1.0 |
| | .500 | 0.0 | 0.0 | 0.0 | 0.0 | 0.0 | 0.0 | | 1.0 | 4.0 | | 1.0 |
| $6h_2$ | 4.000 | 0.0 | 0.0 | 0.0 | 0.0 | 0.0 | 2.0 | | 4.0 | 5.0 | 5.0 | 3.0 |
| | .500 | 0.0 | 0.0 | 0.0 | 0.0 | 0.0 | 0.0 | | 2.0 | 6.0 | 1.0 | 2.0 |
| $6i_2$ | 4.000 | 2.0 | 1.0 | 0.0 | 0.0 | 1.0 | 4.0 | | 2.0 | 9.0 | 6.0 | 7.0 |
| | .500 | 0.0 | 0.0 | 0.0 | 0.0 | 0.0 | 0.0 | | 1.0 | 8.0 | 5.0 | 5.0 |
| $6j_2$ | 4.000 | 0.0 | 0.0 | 0.0 | 2.0 | 2.0 | 3.0 | | 7.0 | 9.0 | | 7.0 |
| | 1.000 | 0.0 | | 0.0 | | | | | 0.0 | | | |
| | .500 | 0.0 | 0.0 | 0.0 | 1.0 | 1.0 | 2.0 | | 3.5 | 7.0 | | 4.0 |
| $6k_2$ | 4.000 | 9.0 | 9.0 | 8.0 | 9.0 | 9.0 | 7.0 | | 8.0 | 9.0 | | 9.0 |
| | 3.000 | 7.0 | 9.0 | 8.0 | 9.0 | 7.0 | 8.0 | | 8.0 | 9.0 | 9.0 | 9.0 |
| | 2.000 | 6.0 | 6.0 | 6.0 | 9.0 | 8.0 | 5.0 | | 9.0 | 9.0 | 9.0 | 9.0 |
| | 1.000 | 3.5 | 3.0 | 5.5 | 9.0 | 9.0 | 9.0 | | 7.5 | 9.0 | | 9.0 |
| | .800 | 5.0 | 6.0 | 5.0 | 9.0 | 9.0 | 7.0 | | 7.0 | 9.0 | | 9.0 |
| | .500 | 3.0 | 6.5 | 3.3 | 8.5 | 8.5 | 9.0 | | 6.0 | 9.0 | 9.0 | 9.0 |
| $6l_2$ | 4.000 | 2.0 | 1.0 | 6.0 | 6.0 | 7.0 | 9.0 | | 8.0 | 9.0 | 9.0 | 7.0 |
| | 1.000 | 0.0 | | 0.0 | | | | | 0.0 | | | |
| | .500 | 0.0 | 0.0 | 0.0 | 0.0 | 2.0 | 7.0 | | 3.0 | 8.0 | | 5.0 |
| $6m_2$ | 4.000 | 0.0 | 0.0 | 0.0 | 0.0 | 1.0 | 2.0 | | 2.0 | 4.0 | | 2.0 |
| | .500 | 0.0 | 0.0 | 0.0 | 0.0 | 1.0 | 0.0 | | 2.0 | 4.0 | | 1.0 |
| $6n_2$ | 4.000 | 3.0 | 2.0 | 6.0 | 2.0 | 1.0 | 8.0 | | 8.0 | 9.0 | | 9.0 |
| | 2.000 | 0.0 | 2.0 | 5.0 | 0.0 | 1.5 | 7.0 | 9.0 | 8.0 | 9.0 | 8.0 | 7.5 |
| | 1.000 | 0.0 | 0.5 | 4.0 | 0.0 | 1.7 | 7.0 | 8.0 | 7.3 | 8.5 | 7.0 | 7.0 |
| | .750 | | | | 0.0 | 0.0 | | 8.0 | 7.0 | 8.0 | 6.0 | 6.0 |
| | .500 | 0.0 | 0.5 | 0.5 | 0.0 | 0.0 | 6.5 | 8.0 | 7.3 | 8.5 | 6.0 | 4.3 |
| $6o_2$ | 4.000 | 0.0 | 0.0 | 0.0 | 0.0 | 2.0 | 1.0 | | 4.0 | 6.0 | 5.0 | 2.0 |
| | .500 | 0.0 | 0.0 | 0.0 | 0.0 | 0.0 | 2.0 | | 4.0 | 7.0 | 4.0 | |
| $6p_2$ | 4.000 | 0.0 | 0.0 | 1.0 | 0.0 | 1.0 | 1.0 | | 0.0 | 0.0 | 0.0 | 0.0 |
| $6r_2$ | 4.000 | 0.0 | 0.0 | 3.0 | 0.0 | 1.0 | 2.0 | | 3.0 | 5.0 | | 1.0 |
| | .500 | 0.0 | 0.0 | 0.0 | 0.0 | 0.0 | 1.0 | | 2.0 | 4.0 | 7.0 | 1.0 |
| $6s_2$ | 4.000 | 0.0 | 0.0 | 0.0 | 0.0 | 0.0 | 1.0 | | 1.0 | 1.0 | 0.0 | 1.0 |
| | .500 | 0.0 | 0.0 | 0.0 | 0.0 | 0.0 | 1.0 | | 1.0 | 1.0 | | 1.0 |
| $6t_2$ | 4.000 | 5.5 | 3.5 | 6.0 | 6.5 | 4.5 | 9.0 | | 8.5 | 9.0 | 8.0 | 9.0 |
| | 2.000 | 5.0 | 3.0 | 2.5 | 5.0 | 0.5 | 8.5 | | 7.5 | 9.0 | 8.0 | 8.5 |
| | 1.000 | 1.3 | 2.0 | 2.3 | 2.0 | 2.0 | 7.5 | | 7.0 | 9.0 | 8.5 | 7.0 |
| | .500 | 0.0 | 1.0 | 0.0 | 0.0 | 0.5 | 6.7 | | 8.0 | 9.0 | 7.0 | 6.0 |
| $6u_2$ | 4.000 | 0.0 | 0.0 | 0.0 | 0.0 | 0.0 | 3.0 | | 2.0 | 9.0 | 1.0 | 3.0 |
| | .500 | 0.0 | 0.0 | 0.0 | 0.0 | 0.0 | 1.0 | | 0.0 | 7.0 | 0.0 | 1.0 |
| $6v_2$ | 4.000 | 0.0 | 2.0 | 2.0 | 0.0 | 0.0 | 4.0 | | 3.0 | 9.0 | 6.0 | 8.0 |
| | .500 | 0.0 | 1.0 | 0.0 | 0.0 | 0.0 | 1.0 | | 1.0 | 6.0 | 0.0 | 6.0 |
| $6w_2$ | 4.000 | 7.5 | 7.5 | 5.0 | 9.0 | 9.0 | 7.5 | | 8.5 | 9.0 | 8.0 | 9.0 |
| | 2.000 | 2.0 | 5.0 | 0.0 | 9.0 | 8.0 | 5.0 | | 8.0 | 9.0 | | 9.0 |
| | 1.000 | 1.0 | 3.0 | 0.0 | 6.0 | 7.0 | 5.0 | | 6.0 | 8.0 | 7.0 | 9.0 |
| | .500 | 2.0 | 2.0 | 0.0 | 2.0 | 4.5 | 4.0 | | 4.5 | 9.0 | 2.5 | 8.0 |
| $6x_2$ | 4.000 | 8.5 | 9.0 | 9.0 | 9.0 | 9.0 | 9.0 | | 9.0 | 9.0 | 8.5 | 9.0 |
| | 2.000 | 6.0 | 9.0 | 4.0 | 9.0 | 9.0 | | | 9.0 | 9.0 | 7.0 | 9.0 |
| | 1.000 | 4.0 | 5.0 | 1.0 | 9.0 | 9.0 | 8.0 | | 8.5 | 9.0 | 7.0 | 9.0 |
| | .500 | 5.7 | 7.0 | 3.0 | 9.0 | 8.0 | 8.5 | | 8.3 | 9.0 | 7.5 | 9.0 |
| $6y_2$ | 4.000 | 2.0 | 0.0 | 6.0 | 0.0 | 0.0 | 4.0 | | 7.0 | 9.0 | 7.0 | 5.0 |
| | .500 | 0.0 | 0.0 | 0.0 | 0.0 | 0.0 | 1.0 | | 5.0 | 8.0 | 4.0 | 2.0 |
| $6z_2$ | 4.000 | 7.0 | 5.0 | 7.0 | 5.0 | 5.0 | 9.0 | | 9.0 | 9.0 | 6.0 | 9.0 |
| | .500 | 2.0 | 0.0 | 0.0 | 0.0 | 0.0 | 7.0 | | 8.0 | 9.0 | 4.0 | 6.0 |
| $6b_3$ | 4.000 | | | | 1.0 | 3.0 | 2.0 | 9.0 | 8.0 | 9.0 | 8.0 | 9.0 |
| | 2.000 | | | | 1.0 | 3.0 | 1.0 | 6.0 | 7.0 | 9.0 | 8.0 | 9.0 |
| | 1.000 | | | | 1.0 | 1.0 | | 3.0 | 7.0 | 9.0 | 7.0 | 8.0 |
| | .500 | | | | | 1.0 | | 3.0 | 7.0 | 9.0 | 7.0 | 6.0 |
| $6c_3$ | 4.000 | | | | 1.0 | 1.0 | 2.0 | 7.0 | 9.0 | 9.0 | 7.0 | 9.0 |
| | 2.000 | | | | | 1.0 | | 6.0 | 7.0 | 9.0 | 7.0 | 8.0 |
| | 1.000 | | | | | | | 6.0 | 7.0 | 9.0 | 7.0 | 7.0 |
| | .500 | | | | | | | 6.0 | 6.0 | 9.0 | 7.0 | 4.0 |
| $6d_3$ | 4.000 | 0.0 | 0.0 | 0.0 | 0.0 | 1.0 | 2.0 | | 5.0 | 9.0 | 7.0 | 5.0 |
| | 2.000 | 0.0 | 0.0 | 0.0 | 0.0 | 0.0 | 3.0 | | 5.0 | 9.0 | 5.0 | 2.0 |
| | 1.000 | 0.0 | 0.0 | 0.0 | 0.0 | 0.0 | 3.0 | | 5.0 | 8.0 | 7.0 | 3.0 |
| | .500 | 0.0 | 0.0 | 0.0 | 0.0 | 0.0 | 5.0 | | 5.0 | 8.0 | 7.0 | 3.0 |
| $6e_3$ | 1.000 | 0.0 | 0.0 | 0.0 | 0.0 | 0.0 | 4.0 | | 0.0 | 4.0 | 0.0 | 1.0 |
| | .500 | 0.0 | 0.0 | 0.0 | 0.0 | 0.0 | 1.0 | | 0.0 | 4.0 | 0.0 | 0.0 |
| | .250 | 0.0 | 0.0 | 0.0 | 0.0 | 0.0 | 1.0 | | 1.0 | 5.0 | 0.0 | 0.0 |
| $6f_3$ | 4.000 | 0.0 | 0.0 | 0.0 | 0.0 | 0.0 | 3.0 | | 6.0 | 9.0 | 2.0 | 2.0 |
| | 2.000 | 0.0 | 0.0 | 0.0 | 0.0 | 0.0 | 2.0 | | 4.0 | 9.0 | 0.0 | 1.5 |
| | 1.000 | 0.0 | 0.0 | 0.0 | 0.0 | 0.0 | 1.0 | | 4.0 | 9.0 | 0.0 | 0.0 |
| | .500 | 0.0 | 0.0 | 0.0 | 0.0 | 0.0 | 4.5 | | 2.0 | 8.0 | 0.0 | 0.0 |
| $6h_3$ | 4.000 | 4.0 | 8.0 | 2.5 | 9.0 | 9.0 | 3.0 | | 4.0 | 9.0 | 7.0 | 7.0 |
| | 2.000 | 6.0 | 6.0 | 4.0 | 9.0 | 9.0 | 9.0 | | 8.0 | 9.0 | 8.0 | 9.0 |
| | 1.000 | 6.0 | 5.0 | 2.0 | 8.0 | 8.0 | 9.0 | | 8.0 | 9.0 | 7.0 | 9.0 |
| | .500 | 6.0 | 4.0 | 0.0 | 7.0 | 5.0 | 5.0 | | 4.0 | 9.0 | 7.0 | 9.0 |
| $6i_3$ | 4.000 | 0.0 | 0.0 | 0.0 | 0.0 | 0.0 | 6.0 | | 3.0 | 9.0 | | 6.0 |
| | .500 | 0.0 | 0.0 | 0.0 | 0.0 | 0.0 | | | 0.0 | 7.0 | 0.0 | 0.0 |

TABLE VI-continued

POST-EMERGENCE TESTS - RATES IN KG/HA

| | | | | | | | | | | | |
|---|---|---|---|---|---|---|---|---|---|---|---|
| 6j₃ | 4.000 | 0.0 | 0.0 | 2.0 | 0.0 | 0.0 | 8.0 | 8.0 | 9.0 | 8.0 | 7.0 |
| | .500 | 0.0 | 0.0 | 0.0 | 0.0 | 0.0 | 8.0 | 8.0 | 9.0 | 7.0 | 0.0 |
| 6k₃ | 4.000 | 0.0 | 0.0 | 0.0 | 0.0 | 0.0 | 0.0 | 0.0 | 6.0 | 0.0 | 0.0 |
| | .500 | 0.0 | 0.0 | 0.0 | 0.0 | 0.0 | 0.0 | 0.0 | 6.0 | 0.0 | 0.0 |
| 6l₃ | 2.000 | 0.0 | 0.0 | 1.0 | 0.0 | 0.0 | 4.0 | 2.0 | 4.0 | 6.0 | 5.0 |
| | 1.000 | 0.0 | 0.0 | 1.0 | 0.0 | 0.0 | 1.0 | 3.0 | 5.0 | 3.0 | 6.0 |
| | .500 | 0.0 | 0.0 | 0.0 | 0.0 | 0.0 | 1.0 | 1.0 | 4.0 | 4.0 | 2.0 |
| 6m₃ | 2.000 | 0.0 | 2.0 | 1.0 | 0.0 | 0.0 | 9.0 | 9.0 | 9.0 | 7.0 | 9.0 |
| | 1.000 | 0.0 | 2.0 | 1.0 | 0.0 | 0.0 | 8.0 | 8.0 | | 6.0 | 9.0 |
| | .500 | 0.0 | 1.0 | 0.0 | 0.0 | 0.0 | 7.0 | 8.0 | 9.0 | 6.0 | 7.0 |
| 6n₃ | 4.000 | 0.0 | 3.0 | 9.0 | 0.0 | 2.0 | 8.0 | 8.0 | 9.0 | 8.0 | 9.0 |
| | 2.000 | 0.0 | 2.0 | 9.0 | 0.0 | 0.0 | 8.0 | 8.0 | 9.0 | 6.0 | 9.0 |
| | 1.000 | 0.0 | 1.0 | 5.0 | 0.0 | 0.0 | | 8.0 | 9.0 | 6.0 | 9.0 |
| | .500 | 0.0 | 0.0 | 1.0 | 0.0 | 0.0 | 5.0 | 8.0 | 6.0 | 5.0 | 8.0 |
| 6o₃ | 4.000 | 7.0 | 5.0 | 2.0 | 8.0 | 6.0 | 7.0 | 7.0 | 9.0 | 8.0 | 9.0 |
| | 2.000 | 5.0 | 3.0 | | 7.0 | 6.0 | 6.0 | 5.0 | 9.0 | 7.0 | 9.0 |
| | 1.000 | 4.0 | 2.0 | | 6.0 | 2.0 | 6.0 | 4.0 | 9.0 | 7.0 | 9.0 |
| | .500 | 1.0 | 1.0 | | 3.0 | 1.0 | 4.0 | 4.0 | 9.0 | 7.0 | 9.0 |
| 6p₃ | 4.000 | 0.0 | 0.0 | 6.0 | 0.0 | 0.0 | 4.0 | 8.0 | 8.0 | | 8.0 |
| | 2.000 | 0.0 | 0.0 | 2.0 | 0.0 | 0.0 | 0.0 | 7.0 | 8.0 | 6.0 | 6.0 |
| | 1.000 | 0.0 | 0.0 | 0.0 | 0.0 | 0.0 | 1.0 | 7.0 | 7.0 | 4.0 | 5.0 |
| | .500 | 0.0 | 0.0 | 0.0 | 0.0 | 0.0 | 0.0 | 6.0 | 7.0 | 1.0 | 4.0 |
| 6q₃ | 4.000 | 1.0 | 0.0 | 0.0 | 0.0 | 0.0 | 2.0 | 2.0 | | 0.0 | 3.0 |
| | .500 | 0.0 | 0.0 | 0.0 | 0.0 | 0.0 | 0.0 | 2.0 | 9.0 | 0.0 | 1.0 |
| 6r₃ | 4.000 | 1.0 | 0.0 | 0.0 | 3.0 | 0.0 | 0.0 | 0.0 | 2.0 | 0.0 | 2.0 |
| | .500 | 0.0 | 0.0 | 0.0 | 0.0 | 0.0 | 0.0 | 0.0 | 2.0 | 0.0 | |
| 6s₃ | 4.000 | 0.0 | 0.0 | 0.0 | 0.0 | 0.0 | 2.0 | 0.0 | 6.0 | 0.0 | 1.0 |
| | .500 | 0.0 | 0.0 | 0.0 | 0.0 | 0.0 | 0.0 | 0.0 | 6.0 | 0.0 | 1.0 |
| 6t₃ | 4.000 | 0.0 | | 0.0 | 0.0 | 0.0 | 0.0 | 0.0 | 5.0 | 0.0 | 3.0 |

| Compound of Example | RATE | BARNY ARDGR | FOXTA IL SP | P NUT SEDGE | WILD OATS | QUACK GRASS | FLD B INDWD | MRNGL RY SP | WILD MUSTD | RAG WEED | VELVE TLEAF |
|---|---|---|---|---|---|---|---|---|---|---|---|
| 10d | 1.000 | 0.0 | 0.0 | 0.0 | 0.0 | 0.0 | 0.0 | 0.0 | | 1.0 | 0.0 |
| | .500 | 0.0 | 0.0 | 0.0 | 0.0 | 0.0 | 0.0 | 0.0 | | 1.0 | 0.0 |
| 10e | 1.000 | 0.0 | 0.0 | 0.0 | 0.0 | 0.0 | 0.0 | 0.0 | | 2.0 | 0.0 |
| | .500 | 0.0 | 0.0 | 0.0 | 0.0 | 0.0 | 0.0 | 0.0 | | 5.0 | 0.0 |
| 10f | 1.000 | 0.0 | 0.0 | 0.0 | 0.0 | 0.0 | 0.0 | 0.0 | | 0.0 | 2.0 |
| | .500 | 0.0 | 0.0 | 0.0 | 0.0 | 0.0 | 0.0 | 0.0 | | 0.0 | 0.0 |
| 10g | 1.000 | 0.0 | 0.0 | 0.0 | 0.0 | 0.0 | 0.0 | 0.0 | | 0.0 | 1.0 |
| | .500 | 0.0 | 0.0 | 0.0 | 0.0 | 0.0 | 0.0 | 0.0 | | 0.0 | 1.0 |
| 10h | 4.000 | 0.0 | 0.0 | 0.0 | 0.0 | 0.0 | 1.0 | 0.0 | | 6.0 | 6.0 |
| | 2.000 | 0.0 | 0.0 | 0.0 | 0.0 | 0.0 | 1.0 | 0.0 | | 4.0 | 8.0 |
| | 1.000 | 0.0 | 0.0 | 0.0 | 0.0 | 0.0 | 1.0 | 0.0 | | 3.0 | 3.0 |
| | .500 | 0.0 | 0.0 | 0.0 | 0.0 | 0.0 | 0.0 | 0.0 | | 2.0 | 2.0 |
| 10i | 4.000 | 0.0 | 0.0 | 0.0 | 0.0 | 0.0 | 0.0 | 0.0 | | 7.0 | 2.0 |
| | 2.000 | 0.0 | 0.0 | 0.0 | 0.0 | 0.0 | 0.0 | 0.0 | | 7.0 | 2.0 |
| | 1.000 | 0.0 | 0.0 | 0.0 | 0.0 | 0.0 | 0.0 | 0.0 | | 8.0 | 2.0 |
| | .500 | 0.0 | 0.0 | 0.0 | 0.0 | 0.0 | 0.0 | 0.0 | | 1.0 | 0.0 |
| 10k | 4.000 | 0.0 | 0.0 | 0.0 | 0.0 | 0.0 | 1.0 | 2.0 | | 8.0 | 9.0 |
| | 2.000 | 0.0 | 0.0 | 0.0 | 0.0 | 0.0 | 1.0 | 1.0 | | 7.0 | 9.0 |
| | 1.000 | 0.0 | 0.0 | 0.0 | 0.0 | 0.0 | 0.0 | 0.0 | | 7.0 | 8.0 |
| | .500 | 0.0 | 0.0 | 0.0 | 0.0 | 0.0 | 0.0 | 0.0 | | 4.0 | 9.0 |
| 10l | 4.000 | 0.0 | 0.0 | 0.0 | 0.0 | 0.0 | 1.0 | 0.0 | | 3.0 | 1.0 |
| | 2.000 | 0.0 | 0.0 | 0.0 | 0.0 | 0.0 | 3.0 | 0.0 | | 2.0 | 0.0 |
| | 1.000 | 0.0 | 0.0 | 0.0 | 0.0 | 0.0 | 0.0 | 0.0 | | 1.0 | 0.0 |
| 10m | 4.000 | 0.0 | 0.0 | 0.0 | 0.0 | 0.0 | 0.0 | 0.0 | | 6.0 | 2.0 |
| | 2.000 | 0.0 | 0.0 | 0.0 | 0.0 | 0.0 | 0.0 | 0.0 | | 5.0 | 1.0 |
| | 1.000 | 0.0 | 0.0 | 0.0 | 0.0 | 0.0 | 0.0 | 0.0 | | 1.0 | 0.0 |
| | .500 | 0.0 | 0.0 | 0.0 | 0.0 | 0.0 | 0.0 | 0.0 | | 2.0 | 0.0 |
| 10n | 4.000 | 6.0 | 9.0 | 7.0 | 3.0 | 4.0 | 2.0 | 6.0 | 9.0 | 9.0 | 9.0 |
| | .500 | 0.0 | 5.0 | 4.0 | 0.0 | 0.0 | 1.0 | 4.0 | 9.0 | 6.0 | 9.0 |
| 10o | 4.000 | 5.0 | 5.0 | 5.0 | 2.0 | 5.0 | 2.0 | 5.0 | 9.0 | 8.0 | 9.0 |
| | .500 | 2.0 | 0.0 | 0.0 | 0.0 | 0.0 | 1.0 | 1.0 | 7.0 | 4.0 | 7.0 |
| 10p | 4.000 | 0.0 | 0.0 | 0.0 | 0.0 | 0.0 | 0.0 | 1.0 | 7.0 | 0.0 | 1.0 |
| | .500 | 0.0 | 0.0 | 0.0 | 0.0 | 0.0 | 0.0 | 0.0 | 5.0 | 0.0 | 0.0 |
| 11a | 4.000 | 2.0 | 1.0 | 0.0 | 0.0 | 1.0 | 5.0 | 4.0 | 9.0 | 7.0 | |
| | .500 | 0.0 | 0.0 | 0.0 | 0.0 | 0.0 | 1.0 | 3.0 | 7.0 | 3.0 | 9.0 |
| 11b | 4.000 | 0.0 | 0.0 | 0.0 | 0.0 | 0.0 | 3.0 | 4.0 | 7.0 | 5.0 | 3.0 |
| | .500 | 0.0 | 0.0 | 0.0 | 0.0 | 0.0 | 0.0 | 0.0 | 0.0 | 3.0 | 1.0 |
| 11c | 4.000 | 0.0 | 0.0 | 0.0 | 0.0 | 0.0 | 1.0 | 2.0 | 7.0 | 4.0 | |
| | .500 | 0.0 | 0.0 | 0.0 | 0.0 | 0.0 | 0.0 | 0.0 | 2.0 | 0.0 | 2.0 |
| 11d | 4.000 | 0.0 | 0.0 | 0.0 | 0.0 | 0.0 | 0.0 | 1.0 | 3.0 | 0.0 | 0.0 |
| | .500 | 0.0 | 0.0 | 0.0 | 0.0 | 0.0 | 0.0 | | 6.0 | | 0.0 |
| 11e | 4.000 | 0.0 | 0.0 | 0.0 | 0.0 | 0.0 | 2.0 | 0.0 | 5.0 | | |
| | .500 | 0.0 | 0.0 | 0.0 | 0.0 | 0.0 | 0.0 | 0.0 | 1.0 | 2.0 | 5.0 |
| 11f | 4.000 | 0.0 | 5.0 | 0.0 | 0.0 | 0.0 | 3.0 | 2.0 | 9.0 | | 9.0 |
| | .500 | 0.0 | 1.0 | 0.0 | 0.0 | 0.0 | 1.0 | 1.0 | 6.0 | 6.0 | 5.0 |
| 11g | 4.000 | 0.0 | 5.0 | 0.0 | 0.0 | 0.0 | 4.0 | 3.0 | 7.0 | 7.0 | 9.0 |
| | .500 | 0.0 | 1.0 | 0.0 | 0.0 | 0.0 | 2.0 | 0.0 | 2.0 | 3.0 | 8.0 |

TABLE VI-continued

| | | | | POST-EMERGENCE TESTS - RATES IN KG/HA | | | | | | | |
|---|---|---|---|---|---|---|---|---|---|---|---|
| 11h | 4.000 | 0.0 | 0.0 | 0.0 | 0.0 | 0.0 | 7.0 | 7.0 | 6.0 | 6.0 | 4.0 |
| | .500 | 0.0 | 0.0 | 0.0 | 0.0 | 0.0 | 1.0 | 2.0 | 2.0 | | 1.0 |
| 11i | 4.000 | 0.0 | 0.0 | 0.0 | 0.0 | 0.0 | 3.0 | 2.0 | 6.0 | | 2.0 |
| | .500 | 0.0 | 0.0 | 0.0 | 0.0 | 0.0 | 1.0 | 1.0 | 4.0 | | 1.0 |
| 18a | 4.000 | 0.0 | 1.0 | 1.0 | 1.0 | 2.0 | 2.0 | 5.0 | 9.0 | 4.0 | 8.0 |
| | 2.000 | 1.0 | 0.0 | 0.0 | 0.0 | 1.0 | 2.0 | 4.0 | 9.0 | 4.0 | 6.0 |
| | 1.000 | 0.0 | 0.0 | 0.0 | 0.0 | 0.0 | 2.0 | 1.0 | 9.0 | 3.0 | 2.0 |
| | .500 | 0.0 | 0.0 | 0.0 | 0.0 | 0.0 | 1.0 | 1.0 | 9.0 | 0.0 | 1.0 |
| 19a | 4.000 | 2.0 | 2.0 | 3.0 | 0.0 | 1.0 | 9.0 | 9.0 | 9.0 | 8.0 | 9.0 |
| | 2.000 | 0.0 | 1.0 | 4.0 | 0.0 | 0.0 | 9.0 | 8.0 | 9.0 | 7.0 | 9.0 |
| | 1.000 | 0.0 | 1.0 | 1.0 | 0.0 | 0.0 | 9.0 | 8.0 | 9.0 | 7.0 | 8.0 |
| | .500 | 0.0 | 0.0 | 0.0 | 0.0 | 0.0 | 5.0 | 6.5 | 9.0 | 7.0 | 7.0 |
| 20a | 4.000 | 0.0 | 2.0 | 7.0 | 0.0 | 5.0 | 5.0 | 1.0 | | 9.0 | 9.0 |
| | 2.000 | 0.0 | 2.0 | 3.0 | 0.0 | 2.0 | 2.0 | 0.0 | | 7.0 | 9.0 |
| | 1.000 | 0.0 | 0.0 | 0.0 | 0.0 | 1.0 | 2.0 | 0.0 | | 7.0 | 9.0 |
| | .500 | 0.0 | 0.0 | 0.0 | 0.0 | 0.0 | 1.0 | 0.0 | | 7.0 | 9.0 |
| 21a | 4.000 | 0.0 | 1.0 | 8.0 | 0.0 | 4.0 | 6.0 | 1.0 | | 9.0 | 9.0 |
| | 2.000 | 0.0 | 0.0 | 1.0 | 0.0 | 1.0 | 2.0 | 0.0 | | 6.0 | 9.0 |
| | 1.000 | 0.0 | 0.0 | 0.0 | 0.0 | 0.0 | 2.0 | 0.0 | | 6.0 | 9.0 |
| | .500 | 0.0 | 0.0 | 0.0 | 0.0 | 0.0 | 1.0 | 0.0 | | 6.0 | 9.0 |
| 21b | 4.000 | 8.0 | 9.0 | 6.0 | 9.0 | 9.0 | 9.0 | 9.0 | 9.0 | 9.0 | 9.0 |
| | 2.000 | 8.0 | 8.0 | 6.0 | 9.0 | 7.0 | 9.0 | 9.0 | 9.0 | 9.0 | 9.0 |
| | 1.000 | 7.0 | 9.0 | 5.0 | 8.0 | 6.0 | 9.0 | 9.0 | 9.0 | 9.0 | 9.0 |
| | .500 | 4.0 | 6.0 | 0.0 | 7.0 | 2.0 | 6.0 | 9.0 | 9.0 | 9.0 | 9.0 |
| 21c | 4.000 | 0.0 | 0.0 | 0.0 | 0.0 | 0.0 | 4.0 | 7.0 | 8.0 | 0.0 | 2.0 |
| | 2.000 | 0.0 | 0.0 | 0.0 | 0.0 | 0.0 | 1.0 | 5.0 | 8.0 | 0.0 | 1.0 |
| | 1.000 | 0.0 | 0.0 | 0.0 | 0.0 | 0.0 | 0.0 | 6.0 | 9.0 | 0.0 | 0.0 |
| | .500 | 0.0 | 0.0 | 0.0 | 0.0 | 0.0 | 0.0 | 5.0 | 9.0 | 0.0 | 0.0 |

EXAMPLE 23

Preemergence herbicidal evaluation of test compounds

The preemergence herbicidal activity of the compounds of the present invention is exemplified by the following tests in which the seeds of a variety of monocotyledonous and dicotyledonous plants are separately mixed with potting soil and planted on top of approximately one inch of soil in separate pint cups. After planting, the cups are sprayed with the selected aqueous acetone solution containing test compound in sufficient quantity to provide the equivalent of about 0.032 kg to 8 kg per hectare of test compound per cup. The treated cups are then placed on greenhouse benches, watered and cared for in accordance with conventional greenhouse procedures. From four to five weeks after treatment, the test are terminated and each cup is examined and rated according to the rating system set forth above. The herbicidal proficiency of the active ingredients of the present invention is evident from the test results which are recorded in Table VII below. Where more than one test is involved for a given compound, the data are averaged.

TABLE VII

| | | | | PRE-EMERGENCE TESTS - RATES IN KG/HA | | | | | | | |
|---|---|---|---|---|---|---|---|---|---|---|---|
| Compound of Example | RATE | BARNY ARDGR | FOXTA IL SP | P NUT SEDGE | WILD OATS | QUACK GRASS | FLD B INDWD | MATRI C SPP | MRNGL RY SP | WILD MUSTD | RAGWE ED | VELVE TLEAF |
| 5a | 2.000 | | | 9.0 | | 4.0 | | 9.0 | 7.0 | 9.0 | 8.0 | 9.0 |
| | 1.500 | | | 2.0 | | 4.0 | | 9.0 | 6.0 | 8.0 | 7.0 | 9.0 |
| | 1.000 | 0.0 | 1.0 | 4.3 | 1.0 | 3.0 | 8.0 | 8.0 | 5.0 | 6.0 | 7.5 | 8.5 |
| | .750 | | | 4.0 | | 1.0 | | 8.0 | 3.0 | 7.0 | 5.0 | 8.0 |
| | .500 | 0.0 | 1.0 | 2.0 | 0.0 | 2.5 | 6.0 | 8.0 | 3.5 | 5.0 | 4.0 | 7.0 |
| 5b | 4.000 | 8.0 | 9.0 | 9.0 | 6.0 | 9.0 | 9.0 | | 9.0 | 9.0 | 9.0 | 9.0 |
| | 2.000 | 8.0 | 9.0 | 9.0 | 6.0 | 9.0 | 9.0 | | 9.0 | 9.0 | 9.0 | 9.0 |
| | 1.000 | 5.0 | 6.0 | 9.0 | 5.0 | 9.0 | 9.0 | | 9.0 | 9.0 | 9.0 | 9.0 |
| | .500 | 4.0 | 9.0 | 9.0 | 6.0 | 9.0 | 9.0 | | 9.0 | 9.0 | 9.0 | 9.0 |
| 5c | 4.000 | 0.0 | 0.0 | 0.0 | 0.0 | 0.0 | 0.0 | | 5.0 | 0.0 | 6.0 | 1.0 |
| | .500 | 0.0 | 0.0 | 0.0 | 0.0 | 0.0 | 0.0 | | 4.0 | 0.0 | 4.0 | 1.0 |
| 5d | 4.000 | 0.0 | 0.0 | 3.0 | 0.0 | 2.0 | 7.0 | | 8.0 | 7.0 | 2.0 | 5.0 |
| | 2.000 | 0.0 | 0.0 | 2.0 | 0.0 | 1.0 | 5.0 | | 6.0 | 9.0 | 4.0 | 1.0 |
| | 1.000 | 0.0 | 0.0 | 5.0 | 0.0 | 2.0 | 4.0 | | 4.0 | 3.0 | 0.0 | 1.0 |
| | .500 | 0.0 | 0.0 | 0.0 | 0.0 | 0.0 | 2.0 | | 2.0 | 0.0 | 0.0 | 0.0 |
| 5e | 4.000 | 8.5 | 9.0 | 9.0 | 8.0 | 9.0 | 9.0 | | 8.5 | 9.0 | 8.5 | 8.5 |
| | 2.000 | 8.0 | 9.0 | 9.0 | 7.5 | 9.9 | 9.0 | | 7.0 | 9.0 | 9.0 | 9.0 |
| | 1.000 | 8.5 | 7.0 | 9.0 | 7.0 | 9.0 | 9.0 | | 9.0 | 9.0 | 9.0 | 9.0 |
| | .500 | 5.5 | 6.0 | 9.0 | 6.6 | 9.0 | 8.0 | | 8.0 | 9.0 | 9.0 | 8.0 |
| 5f | 4.000 | 8.0 | 7.0 | 9.0 | 6.0 | 9.0 | 9.0 | | 9.0 | 9.0 | 9.0 | 9.0 |
| | 2.000 | 3.0 | 3.0 | 9.0 | 6.0 | 9.0 | 9.0 | | 9.0 | 9.0 | 9.0 | 9.0 |
| | 1.000 | 3.0 | 7.0 | 9.0 | 2.0 | 6.0 | 9.0 | | 9.0 | 9.0 | 9.0 | 9.0 |
| | .500 | 0.0 | 5.0 | 9.0 | 0.0 | 5.0 | 9.0 | | 9.0 | 9.0 | 7.0 | 9.0 |
| 5g | 4.000 | 1.0 | 0.0 | 8.0 | 4.0 | 1.0 | 8.0 | | 9.0 | 9.0 | 9.0 | 9.0 |
| | 2.000 | 2.0 | 2.0 | 6.0 | 2.0 | 0.0 | 6.0 | | 8.0 | 8.0 | 7.0 | 8.0 |
| | 1.000 | 1.0 | 1.0 | 6.0 | 2.0 | 1.0 | 5.0 | | 8.0 | 9.0 | 6.0 | 9.0 |
| | .500 | 0.0 | 0.0 | 2.0 | 0.0 | 0.0 | 2.0 | | 8.0 | 5.0 | 4.0 | 4.0 |
| 5h | 1.000 | 6.0 | 6.0 | 9.0 | 4.0 | 4.0 | 9.0 | | 9.0 | 9.0 | 9.0 | 9.0 |
| | .500 | 3.0 | 5.0 | 9.0 | 0.0 | 4.0 | 9.0 | | 9.0 | 9.0 | 9.0 | 9.0 |

TABLE VII-continued

PRE-EMERGENCE TESTS - RATES IN KG/HA

| | | | | | | | | | | | | |
|---|---|---|---|---|---|---|---|---|---|---|---|---|
| 6a₁ | 4.000 | 3.6 | 4.6 | 9.0 | 3.4 | 8.6 | 9.0 | 9.0 | 8.1 | 8.6 | 8.2 | 8.7 |
| | 2.000 | 2.9 | 3.6 | 8.7 | 2.4 | 7.4 | 8.8 | 8.3 | 7.6 | 7.9 | 7.2 | 8.4 |
| | 1.500 | | | 4.0 | | 4.0 | | 9.0 | 7.0 | 8.0 | 4.0 | 9.0 |
| | 1.000 | 1.0 | 2.7 | 7.3 | 1.1 | 6.1 | 8.3 | 7.5 | 6.3 | 7.7 | 7.2 | 8.4 |
| | .750 | | | 7.0 | 0.0 | 1.0 | | 8.0 | 5.5 | 7.0 | 6.0 | 8.5 |
| | .600 | | | | | | | 9.0 | 8.0 | 9.0 | 8.0 | 9.0 |
| | .500 | 0.5 | 1.4 | 7.1 | 1.0 | 4.7 | 8.0 | 7.3 | 5.2 | 7.3 | 6.0 | 7.7 |
| 6b₁ | 4.000 | 0.0 | 0.0 | 5.0 | 0.0 | 1.0 | 3.0 | | 4.0 | | 6.0 | 8.0 |
| | 2.000 | 0.0 | 0.0 | 4.0 | 0.0 | 0.0 | 2.0 | | 3.0 | | 5.0 | 8.0 |
| | 1.000 | 0.0 | 0.0 | 0.0 | 0.0 | 0.0 | 0.0 | | 1.0 | | 3.0 | 4.0 |
| | .500 | 0.0 | 0.0 | 0.0 | 0.0 | 0.0 | 0.0 | | 0.0 | | 2.0 | 4.0 |
| 6c₁ | 4.000 | 1.5 | 1.5 | 1.0 | 3.5 | 4.5 | 2.0 | | 5.0 | 5.0 | 5.0 | 2.5 |
| | 2.000 | 0.5 | 0.0 | 0.0 | 0.0 | 0.0 | 1.0 | | 2.5 | 3.0 | 4.5 | 1.5 |
| | 1.000 | 0.0 | 0.0 | 0.0 | 0.0 | 0.0 | 0.0 | | 1.5 | 2.0 | 2.0 | 1.5 |
| | .500 | 0.0 | 0.0 | 0.0 | 0.0 | 0.0 | 0.0 | | 1.0 | 0.0 | 0.0 | 0.5 |
| 5d₁ | 4,000 | 3.0 | | 9.0 | 0.0 | 3.0 | 9.0 | | 8.0 | 8.0 | 8.0 | 6.0 |
| | 1.000 | 0.0 | 0.0 | 5.0 | 2.0 | 0.0 | 9.0 | | 5.0 | | 5.0 | 5.0 |
| | .500 | 0.0 | 0.0 | 4.0 | 0.0 | 0.0 | 5.0 | | 4.0 | | | 5.0 |
| 6e₁ | 1.000 | 0.0 | 0.0 | 2.0 | 0.0 | 0.0 | 1.0 | | 3.0 | | 0.0 | 2.0 |
| | .500 | 0.0 | 0.0 | 0.0 | 0.0 | 0.0 | 0.0 | | 1.0 | | 0.0 | 1.0 |
| 6f₁ | 4.000 | 1.5 | 1.5 | 1.0 | 3.5 | 4.5 | 2.0 | | 5.0 | 5.0 | 5.0 | 2.5 |
| | 2.000 | 0.5 | 0.0 | 0.0 | 0.0 | 0.0 | 1.0 | | 2.5 | 3.0 | 4.5 | 1.5 |
| | 1.000 | 0.0 | 0.0 | 0.0 | 0.0 | 0.0 | 0.0 | | 1.5 | 2.0 | 2.0 | 1.5 |
| | .500 | 0.0 | 0.0 | 0.0 | 0.0 | 0.0 | 0.0 | | 1.0 | 0.0 | 0.0 | 0.5 |
| 6g₁ | 4.000 | 2.0 | 2.0 | 9.0 | 8.0 | 9.0 | 7.0 | | 9.0 | | 9.0 | 9.0 |
| | 2.000 | 6.0 | 2.0 | 9.0 | 7.0 | 9.0 | 9.0 | | 9.0 | | 9.0 | 9.0 |
| | 1.000 | 1.0 | 0.0 | 2.0 | 4.0 | 2.0 | 3.0 | | 9.0 | | 9.0 | 8.0 |
| | .500 | 3.0 | 2.0 | 6.0 | 5.0 | 8.0 | 7.0 | | 9.0 | | 7.0 | 8.0 |
| 6h₁ | 4.000 | 2.0 | 2.0 | 9.0 | 8.0 | 9.0 | 7.0 | | 9.0 | | 9.0 | 9.0 |
| | 2.000 | 6.0 | 2.0 | 9.0 | 7.0 | 9.0 | 9.0 | | 9.0 | | 9.0 | 9.0 |
| | 1.000 | 1.0 | 0.0 | 2.0 | 4.0 | 2.0 | 3.0 | | 9.0 | | 9.0 | 8.0 |
| | .500 | 3.0 | 2.0 | 6.0 | 5.0 | 8.0 | 7.0 | | 9.0 | | 7.0 | 8.0 |
| 6i₁ | 4.000 | 8.0 | 4.0 | 9.0 | 6.0 | 9.0 | 9.0 | | 7.0 | 9.0 | 6.0 | 9.0 |
| | 2.000 | 6.0 | 7.0 | 6.0 | 3.0 | 9.0 | 8.0 | | 7.0 | 9.0 | 4.0 | 9.0 |
| | 1.000 | 6.0 | 6.0 | 9.0 | 5.0 | 9.0 | 9.0 | | 4.0 | 9.0 | 6.0 | 9.0 |
| | .500 | 2.0 | 3.0 | 9.0 | 3.0 | 9.0 | 5.0 | | 4.0 | 9.0 | 4.0 | 9.0 |
| 6j₁ | 4.000 | 6.1 | 8.1 | 9.0 | 7.4 | 9.0 | 9.0 | | 9.0 | 9.0 | 8.3 | 9.0 |
| | 3.000 | 8.0 | 7.0 | 9.0 | 7.0 | 9.0 | 9.0 | | 9.0 | 9.0 | 7.0 | 9.0 |
| | 2.000 | 7.0 | 7.3 | 9.0 | 7.4 | 8.9 | 9.0 | 9.0 | 8.6 | 8.9 | 8.3 | 8.8 |
| | 1.000 | 4.9 | 6.7 | 9.0 | 6.9 | 9.0 | 8.8 | 8.8 | 7.8 | 8.9 | 8.4 | 8.6 |
| | .800 | 5.0 | 6.0 | 9.0 | 5.0 | 9.0 | 9.0 | | 8.0 | 9.0 | 5.0 | 8.0 |
| | .500 | 3.6 | 5.1 | 8.7 | 5.5 | 8.7 | 8.1 | 8.8 | 7.1 | 8.8 | 7.6 | 8.1 |
| 6k₁ | 4.000 | 0.0 | 3.0 | 4.0 | 0.0 | 2.0 | 1.0 | | 3.0 | 3.0 | 2.0 | 1.0 |
| | .500 | 0.0 | 0.0 | 3.0 | 0.0 | 0.0 | 0.0 | | 2.0 | 3.0 | 2.0 | 1.0 |
| 6l₁ | 4.000 | 0.0 | 0.0 | 4.0 | 0.0 | 4.0 | 1.0 | | 5.0 | 7.0 | 3.0 | 8.0 |
| | .500 | 0.0 | 0.0 | 2.0 | 0.0 | 3.0 | 1.0 | | 2.0 | 3.0 | 2.0 | 7.0 |
| 6m₁ | 4.000 | 5.0 | 6.0 | 9.0 | 7.0 | 9.0 | 9.0 | | 9.0 | 9.0 | 7.0 | 9.0 |
| | 2.000 | 9.0 | 9.0 | 9.0 | 8.0 | 9.0 | 9.0 | | 9.0 | 9.0 | 9.0 | 9.0 |
| | 1.000 | 6.7 | 8.5 | 9.0 | 6.5 | 9.0 | 9.0 | | 8.3 | 9.0 | 8.0 | 9.0 |
| | .500 | 4.0 | 5.5 | 8.6 | 5.8 | 9.0 | 7.5 | | 8.4 | 8.5 | 7.3 | 8.5 |
| | .250 | 4.3 | 6.3 | 7.8 | 6.0 | 9.0 | 8.3 | | 7.5 | 9.0 | 4.7 | 8.7 |
| 6n₁ | 4.000 | 0.0 | 4.0 | 9.0 | 4.0 | 7.0 | 9.0 | | 8.0 | 9.0 | 8.0 | 9.0 |
| | 3.000 | 0.0 | 3.0 | 9.0 | 3.0 | 9.0 | 9.0 | | 8.0 | 9.0 | 9.0 | 9.0 |
| | 2.000 | 0.0 | 7.0 | 9.0 | 2.0 | 9.0 | 9.0 | | 8.0 | 9.0 | 9.0 | 9.0 |
| | 1.000 | 0.0 | 2.0 | 9.0 | 1.0 | 7.0 | 9.0 | | 8.0 | 8.0 | 8.0 | 9.0 |
| | .800 | 0.0 | 2.0 | 9.0 | 2.0 | 9.0 | 9.0 | | 8.0 | 8.0 | 9.0 | 9.0 |
| | .500 | 0.0 | 0.0 | 8.0 | 1.0 | 6.0 | 9.0 | | 8.0 | 9.0 | 9.0 | 9.0 |
| 6o₁ | 4.000 | 3.0 | 2.0 | 7.0 | 0.0 | 8.0 | 9.0 | | 9.0 | 9.0 | 8.0 | 6.0 |
| | .500 | 0.0 | 0.0 | 1.0 | 0.0 | 8.0 | 3.0 | | 4.0 | 7.0 | 2.0 | 2.0 |
| 6q₁ | 4.000 | 0.5 | 0.0 | 9.0 | 0.5 | 4.5 | 9.0 | | 9.0 | 9.0 | 8.0 | 9.0 |
| | 2.000 | 1.0 | 0.0 | 8.0 | 0.0 | 4.0 | 9.0 | | 9.0 | 9.0 | 5.0 | 9.0 |
| | 1.000 | 0.0 | 0.0 | 8.0 | 0.0 | 3.0 | 9.0 | | 9.0 | 9.0 | 4.0 | 7.0 |
| | .500 | 0.0 | 0.0 | 5.0 | 0.0 | 1.5 | 5.5 | | 8.0 | 9.0 | 3.0 | 8.0 |
| 6r₁ | 4.000 | 8.0 | 9.0 | 9.0 | 8.0 | 9.0 | 9.0 | | 9.0 | 9.0 | 8.0 | 9.0 |
| | 1.000 | 2.0 | 2.0 | 9.0 | 4.0 | 9.0 | 3.0 | | 6.0 | 9.0 | 9.0 | 7.0 |
| | .500 | 2.0 | 1.5 | 8.5 | 3.5 | 9.0 | 4.0 | | 5.5 | 9.0 | 4.0 | 7.5 |
| 6s₁ | 4.000 | 5.0 | 5.0 | 9.0 | 6.0 | 9.0 | 9.0 | | 9.0 | 9.0 | 9.0 | 9.0 |
| | 1.000 | 1.0 | 1.0 | 7.0 | 1.0 | 9.0 | 9.0 | | 9.0 | 9.0 | 4.0 | 9.0 |
| | .500 | 3.5 | 1.0 | 9.0 | 3.0 | 8.0 | 9.0 | | 9.0 | 9.0 | 6.0 | 9.0 |
| 6t₁ | 4.000 | 5.0 | 2.5 | 9.0 | 7.5 | 9.0 | 9.0 | | 9.0 | 9.0 | 9.0 | 9.0 |
| | 2.000 | 3.0 | 6.0 | 9.0 | 8.0 | 9.0 | 9.0 | | 9.0 | 9.0 | 9.0 | 7.0 |
| | 1.000 | 0.0 | 0.0 | 8.0 | 6.0 | 9.0 | 9.0 | | 9.0 | 9.0 | 8.0 | 6.0 |
| | .500 | 1.0 | 0.5 | 4.5 | 5.0 | 8.0 | 7.0 | | 9.0 | 8.5 | 5.0 | 5.5 |
| 6u₁ | 4.000 | 1.0 | 0.0 | 9.0 | 2.0 | 5.0 | 9.0 | | 9.0 | 9.0 | 9.0 | 6.0 |
| | 1.000 | 0.0 | 0.0 | 0.0 | 0.0 | 0.0 | 0.0 | | 7.0 | 9.0 | 2.0 | 1.0 |
| | .500 | 0.5 | 0.0 | 4.5 | 1.0 | 1.5 | 1.5 | | 4.5 | 7.0 | 2.5 | 3.5 |
| 6v₁ | 4.000 | 0.0 | 1.0 | 0.0 | 1.0 | 1.0 | 2.0 | | 6.0 | 3.0 | 0.0 | 2.0 |
| | .500 | 0.0 | 0.0 | 0.0 | 0.0 | 1.0 | 4.0 | | 6.0 | 1.0 | 2.0 | 1.0 |
| 6w₁ | 4.000 | 0.5 | 5.0 | 9.0 | 0.5 | 8.0 | 9.0 | | 9.0 | 8.5 | 6.5 | 9.0 |
| | 2.000 | 0.0 | 0.0 | 9.0 | 0.0 | 5.0 | 9.0 | | 9.0 | 9.0 | 5.0 | 8.0 |
| | 1.000 | 0.0 | 0.0 | 6.0 | 0.0 | 1.0 | 9.0 | | 8.0 | 7.0 | 2.0 | 5.0 |

TABLE VII-continued

PRE-EMERGENCE TESTS - RATES IN KG/HA

| | | | | | | | | | | | | |
|---|---|---|---|---|---|---|---|---|---|---|---|---|
| | .500 | 0.0 | 0.0 | 5.5 | 0.5 | 2.5 | 9.0 | | 8.5 | 7.0 | 3.0 | 5.0 |
| 6x$_1$ | 4.000 | 0.0 | 0.0 | 6.0 | 1.0 | 9.0 | 9.0 | | 9.0 | 6.0 | 2.0 | 4.0 |
| | .500 | 0.0 | 0.0 | 5.0 | 1.0 | 2.0 | 6.0 | | 4.0 | 4.0 | 2.0 | 1.0 |
| 6y$_1$ | 4.000 | 2.0 | 1.0 | 9.0 | 6.0 | 9.0 | 8.0 | | 9.0 | 9.0 | 9.0 | 8.0 |
| | .500 | 6.0 | 0.0 | 5.0 | 1.0 | 7.0 | 8.0 | | 6.0 | 9.0 | 4.0 | 7.0 |
| 6z$_1$ | 4.000 | 0.5 | 0.0 | 1.5 | 0.5 | 0.5 | 0.5 | | 2.5 | 1.0 | 1.0 | 2.0 |
| | .500 | 0.0 | 0.0 | 1.0 | 0.0 | 0.0 | 0.0 | | 3.0 | 1.0 | 1.5 | 2.0 |
| 6a$_2$ | 4.000 | 0.0 | 2.0 | 3.0 | 0.0 | 4.0 | 9.0 | | 9.0 | 9.0 | 1.0 | 8.0 |
| | .500 | 0.0 | 1.0 | 9.0 | 0.0 | 1.0 | 9.0 | | 7.0 | 9.0 | 2.0 | 8.0 |
| 6b$_2$ | 4.000 | 0.0 | 2.0 | 0.0 | 0.0 | 0.0 | 0.0 | | 5.0 | 6.0 | 2.0 | 6.0 |
| | .500 | 0.0 | 0.0 | 0.0 | 0.0 | 0.0 | 0.0 | | 5.0 | 9.0 | 1.0 | 6.0 |
| 6c$_2$ | 4.000 | 5.0 | 5.0 | 9.0 | 7.0 | 9.0 | 9.0 | | 9.0 | 9.0 | 9.0 | 9.0 |
| | 1.000 | 3.0 | 5.0 | 9.0 | 4.0 | 9.0 | 9.0 | | 5.0 | 9.0 | 7.0 | 9.0 |
| | .500 | 2.0 | 2.0 | 8.0 | 5.0 | 9.0 | 9.0 | | 6.0 | 9.0 | 7.0 | 8.5 |
| 6d$_2$ | 4.000 | 0.0 | 1.0 | 6.0 | 0.0 | 0.0 | 3.0 | | 1.0 | 8.0 | 0.0 | 7.0 |
| | .500 | 0.0 | 0.0 | 0.0 | 0.0 | 0.0 | 2.0 | | 0.0 | 1.0 | 0.0 | 1.0 |
| 6e$_2$ | 4.000 | 0.0 | 0.0 | 6.0 | 1.0 | 7.0 | 1.0 | | 7.0 | 8.0 | 7.0 | 3.0 |
| | .500 | 0.0 | 0.0 | 2.0 | 1.0 | 4.0 | 1.0 | | 5.0 | 2.0 | 2.0 | 2.0 |
| 6f$_2$ | 4.000 | 0.0 | 0.0 | 0.0 | 0.0 | 1.0 | 1.0 | | 4.0 | 7.0 | 2.0 | 3.0 |
| | .500 | 0.0 | 0.0 | 0.0 | 0.0 | 0.0 | 0.0 | | 2.0 | 6.0 | 2.0 | 1.0 |
| 6g$_2$ | 4.000 | 0.0 | 1.0 | 5.0 | 2.0 | 4.0 | 2.0 | | 5.0 | 6.0 | 2.0 | 5.0 |
| | .500 | 0.0 | 0.0 | 1.0 | 1.0 | 2.0 | 3.0 | | 2.0 | 5.0 | 2.0 | 4.0 |
| 6h$_2$ | 4.000 | 1.0 | 0.0 | 6.0 | 0.0 | 0.0 | 7.0 | | 6.0 | 5.0 | 2.0 | 5.0 |
| | .500 | 0.0 | 0.0 | 4.0 | 0.0 | 0.0 | 4.0 | | 5.0 | 4.0 | 2.0 | 3.0 |
| 6i$_2$ | 4.000 | 1.0 | 0.0 | 2.0 | 2.0 | 4.0 | 6.0 | | 5.0 | 7.0 | 1.0 | 4.0 |
| | .500 | 3.0 | 0.0 | 3.0 | 1.0 | 0.0 | 3.0 | | 3.0 | 6.0 | 0.0 | 1.0 |
| 6j$_2$ | 4.000 | 3.0 | 2.0 | 7.0 | 3.0 | 9.0 | 9.0 | | 8.0 | 8.0 | 5.0 | 8.0 |
| | .500 | 0.0 | 0.0 | 3.0 | 0.0 | 4.0 | 4.0 | | 5.0 | 5.0 | 0.0 | 5.0 |
| 6k$_2$ | 4.000 | 9.0 | 9.0 | 9.0 | 9.0 | 9.0 | 9.0 | | 9.0 | 9.0 | 9.0 | 9.0 |
| | 3.000 | 9.0 | 9.0 | 9.0 | 9.0 | 9.0 | 9.0 | | 9.0 | 9.0 | 9.0 | 9.0 |
| | 2.000 | 9.0 | 9.0 | 9.0 | 6.0 | 9.0 | 9.0 | | 9.0 | 9.0 | 9.0 | 9.0 |
| | 1.000 | 5.5 | 9.0 | 9.0 | 6.0 | 9.0 | 9.0 | | 8.0 | 9.0 | 8.0 | 9.0 |
| | .800 | 9.0 | 9.0 | 9.0 | 6.0 | 9.0 | 9.0 | | 9.0 | 9.0 | 7.0 | 9.0 |
| | .500 | 4.3 | 7.5 | 9.0 | 6.5 | 9.0 | 9.0 | | 8.0 | 9.0 | 8.0 | 9.0 |
| 6l$_2$ | 4.000 | 7.0 | 7.0 | 9.0 | 5.0 | 9.0 | 8.0 | | 9.0 | 9.0 | 7.0 | 9.0 |
| | .500 | 4.0 | 4.0 | 9.0 | 1.0 | 9.0 | 8.0 | | 4.0 | 9.0 | 2.0 | 5.0 |
| 6m$_2$ | 4.000 | 3.0 | 2.0 | 8.0 | 1.0 | 7.0 | 8.0 | | 6.0 | 7.0 | 6.0 | 7.0 |
| | .500 | 0.0 | 0.0 | 3.0 | 0.0 | 9.0 | 4.0 | | 5.0 | 6.0 | 4.0 | 5.0 |
| 6n$_2$ | 4.000 | 5.0 | 5.0 | 9.0 | 6.0 | 9.0 | 9.0 | | 9.0 | 9.0 | 9.0 | 9.0 |
| | 2.000 | 2.0 | 4.0 | 9.0 | 0.5 | 9.0 | 9.0 | 9.0 | 8.5 | 9.0 | 6.0 | 9.0 |
| | 1.000 | 3.0 | 4.0 | 9.0 | 1.0 | 6.3 | 9.0 | 9.0 | 8.5 | 8.8 | 7.7 | 8.5 |
| | .750 | | | | 0.0 | 0.0 | | 8.0 | 6.0 | 5.0 | | 7.0 |
| | .600 | | | | | | | 9.0 | 9.0 | 9.0 | 8.0 | 9.0 |
| | .500 | 1.3 | 2.0 | 7.7 | 0.3 | 3.3 | 9.0 | 8.0 | 8.3 | 8.0 | 5.0 | 7.5 |
| 6o$_2$ | 4.000 | 6.0 | 6.0 | 9.0 | 4.0 | 9.0 | 9.0 | | 5.0 | 5.0 | 0.0 | 7.0 |
| | .500 | 0.0 | 1.0 | 2.0 | 0.0 | 0.0 | 2.0 | | 3.0 | 6.0 | 0.0 | 7.0 |
| 6p$_2$ | 4.000 | 0.0 | 0.0 | 0.0 | 0.0 | 0.0 | 1.0 | | 2.0 | 0.0 | 0.0 | 0.0 |
| 6q$_2$ | 4.000 | 0.0 | 0.0 | 1.0 | 0.0 | 1.0 | 3.0 | | 6.0 | 0.0 | 0.0 | 2.0 |
| | .500 | 0.0 | 0.0 | 2.0 | 0.0 | 0.0 | 0.0 | | 0.0 | 0.0 | 0.0 | 0.0 |
| 6r$_2$ | 4.000 | 2.0 | 0.0 | 7.0 | 2.0 | 4.0 | 6.0 | | 6.0 | 6.0 | 4.0 | 5.0 |
| | .600 | | | | | | | 0.0 | 0.0 | 0.0 | 1.0 | 0.0 |
| | .500 | 0.0 | 0.0 | 5.0 | 0.0 | 2.0 | 2.0 | | 6.0 | 0.0 | 5.0 | 2.0 |
| 6s$_2$ | 4.000 | 0.0 | 0.0 | 4.0 | 0.0 | 1.0 | 2.0 | | 0.0 | 0.0 | 0.0 | 0.0 |
| | .500 | 0.0 | 0.0 | 0.0 | 0.0 | 0.0 | 2.0 | | 0.0 | 0.0 | 0.0 | 0.0 |
| 6t$_2$ | 4.000 | 7.5 | 6.0 | 9.0 | 6.5 | 9.0 | 9.0 | | 9.0 | 9.0 | 9.0 | 9.0 |
| | 2.000 | 7.5 | 5.5 | 9.0 | 4.5 | 9.0 | 9.0 | | 9.0 | 9.0 | 8.5 | 9.0 |
| | 1.000 | 3.3 | 4.5 | 9.0 | 4.5 | 7.5 | 9.0 | | 8.7 | 9.0 | 8.0 | 8.5 |
| | .500 | 2.7 | 3.0 | 7.3 | 3.5 | 6.0 | 9.0 | | 8.7 | 9.0 | 8.0 | 7.0 |
| 6u$_2$ | 4.000 | 0.0 | 0.0 | 0.0 | 0.0 | 0.0 | 0.0 | | 5.0 | 8.0 | 0.0 | 1.0 |
| | .500 | 0.0 | 0.0 | 0.0 | 0.0 | 0.0 | 0.0 | | 1.0 | 9.0 | 0.0 | 1.0 |
| 6v$_2$ | 4.000 | 0.0 | 0.0 | 8.0 | 0.0 | 3.0 | 1.0 | | 6.0 | 9.0 | 4.0 | 9.0 |
| | .500 | 0.0 | 0.0 | 7.0 | 0.0 | 0.0 | 0.0 | | 0.0 | 2.0 | 0.0 | 2.0 |
| 6w$_2$ | 4.000 | 6.5 | 7.0 | 9.0 | 7.0 | 8.0 | 9.0 | | 8.0 | 9.0 | 8.5 | 9.0 |
| | 2.000 | 7.0 | 9.0 | 9.0 | 7.0 | 9.0 | 9.0 | | 8.0 | 9.0 | 9.0 | 9.0 |
| | 1.000 | 7.0 | 6.0 | 9.0 | 6.0 | 9.0 | 8.0 | | 8.0 | 9.0 | 8.0 | 8.0 |
| | .500 | 3.5 | 1.5 | 8.0 | 4.5 | 9.0 | 9.0 | | 7.0 | 9.0 | 5.5 | 8.5 |
| 6x$_2$ | 4.000 | 9.0 | 9.0 | 9.0 | 7.5 | 9.0 | 9.0 | | 9.0 | 9.0 | 9.0 | 9.0 |
| | 2.000 | 9.0 | 9.0 | 9.0 | 8.0 | 9.0 | 9.0 | | 9.0 | 9.0 | 9.0 | 9.0 |
| | 1.000 | 5.0 | 9.0 | 8.5 | 7.0 | 9.0 | 9.0 | | 8.5 | 9.0 | 9.0 | 9.0 |
| 6y$_2$ | 4.000 | 1.0 | 4.0 | 3.0 | 4.0 | 2.0 | 4.0 | | 8.0 | 9.0 | 6.0 | 8.0 |
| | .500 | 0.0 | 1.0 | 3.0 | 0.0 | 4.0 | 9.0 | | 8.0 | 9.0 | 8.0 | 7.0 |
| 6z$_2$ | 4.000 | 4.0 | 7.0 | 9.0 | 7.0 | 9.0 | 9.0 | | 9.0 | 9.0 | 9.0 | 9.0 |
| | .500 | 0.0 | 1.0 | 0.0 | 0.0 | 7.0 | 3.0 | | 8.0 | 7.0 | 1.0 | 7.0 |
| 6a$_3$ | 2.000 | 0.0 | 0.0 | 3.0 | 1.0 | 1.0 | 0.0 | | 3.0 | 3.0 | 2.0 | 2.0 |
| | 1.000 | 0.0 | 0.0 | 1.0 | 0.0 | 0.0 | 0.0 | | 7.0 | 0.0 | 6.0 | 0.0 |
| | .500 | 0.0 | 0.0 | 0.0 | 0.0 | 0.0 | 0.0 | | 7.0 | 5.0 | 0.0 | 5.0 |
| 6c$_3$ | 4.000 | | | | 1.0 | 1.0 | 2.0 | 7.0 | 9.0 | 9.0 | 7.0 | 9.0 |
| | 2.000 | | | | | 1.0 | | 6.0 | 7.0 | 9.0 | 7.0 | 8.0 |
| | 1.000 | | | | | | | 6.0 | 7.0 | 9.0 | 7.0 | 7.0 |
| | .500 | | | | | | | 6.0 | 6.0 | 9.0 | 7.0 | 4.0 |
| 6d$_3$ | 4.000 | 1.0 | 0.0 | 9.0 | 2.0 | 9.0 | 9.0 | | 8.0 | 6.0 | 8.0 | 3.0 |

TABLE VII-continued
PRE-EMERGENCE TESTS - RATES IN KG/HA

|  | | | | | | | | | | | |
|---|---|---|---|---|---|---|---|---|---|---|---|
|  | 2.000 | 0.0 | 0.0 | 9.0 | 0.0 | 9.0 | 9.0 |  | 7.0 | 6.0 | 7.0 | 1.0 |
|  | 1.000 | 0.0 | 0.0 | 0.0 | 0.0 | 9.0 | 9.0 |  | 7.0 | 7.0 | 0.0 | 2.0 |
|  | .500 | 0.0 | 0.0 | 0.0 | 0.0 | 9.0 | 9.0 |  | 6.0 | 9.0 | 0.0 | 1.0 |
| 6e$_3$ | 2.000 | 2.0 | 0.0 | 2.0 | 1.0 | 0.0 | 6.0 |  | 6.0 |  | 3.0 | 2.0 |
|  | 1.000 | 0.0 | 0.0 | 1.0 | 0.0 | 0.0 | 0.0 |  | 3.0 |  | 1.0 | 3.0 |
|  | .500 | 0.0 | 0.0 | 9.0 | 0.0 | 0.0 |  |  | 5.0 |  | 0.0 | 3.0 |
| 6f$_3$ | 4.000 | 0.0 | 0.0 | 8.0 | 1.0 | 5.0 | 8.0 |  | 8.5 | 6.0 | 7.5 | 4.5 |
|  | 2.000 | 0.0 | 0.0 | 3.5 | 0.0 | 1.5 | 5.5 |  | 8.5 | 6.0 | 4.5 | 1.0 |
|  | 1.000 | 0.0 | 0.0 | 2.0 | 0.0 | 1.5 | 5.0 |  | 7.0 | 6.0 | 2.0 | 3.0 |
|  | .500 | 0.0 | 0.0 | 1.5 | 0.0 | 0.5 | 1.0 |  | 3.5 | 1.0 | 0.0 | 0.0 |
| 6g$_3$ | 4.000 | 0.0 | 0.0 | 0.0 | 0.0 | 0.0 | 2.0 |  | 3.0 | 0.0 | 3.0 | 1.0 |
|  | .500 | 0.0 | 0.0 | 0.0 | 0.0 | 0.0 |  |  | 5.0 | 0.0 | 0.0 |  |
| 6h$_3$ | 4.000 | 8.0 | 7.0 | 9.0 | 8.5 | 9.0 | 9.0 |  | 8.5 | 8.0 | 8.5 | 8.5 |
|  | 2.000 | 5.0 | 6.0 | 9.0 | 6.5 | 9.0 | 9.0 |  | 9.0 | 9.0 | 9.0 | 9.0 |
|  | 1.000 | 5.5 | 6.0 | 9.0 | 7.5 | 9.0 | 9.0 |  | 9.0 | 9.0 | 9.0 | 9.0 |
|  | .500 | 5.0 | 4.0 | 9.0 | 6.5 | 9.0 | 7.0 |  | 8.0 | 9.0 | 9.0 | 8.0 |
| 6i$_3$ | 4.000 | 0.0 | 0.0 | 1.0 | 0.0 | 1.0 | 1.0 |  | 7.0 | 7.0 | 3.0 | 4.0 |
|  | .500 | 0.0 | 0.0 | 0.0 | 0.0 | 0.0 | 0.0 |  | 7.0 | 3.0 | 0.0 | 1.0 |
| 6j$_3$ | 4.000 | 0.0 | 0.0 | 9.0 | 0.0 | 5.0 | 9.0 |  | 9.0 | 9.0 | 9.0 | 7.0 |
|  | .500 | 0.0 | 0.0 | 9.0 | 0.0 | 0.0 | 9.0 |  | 8.0 | 9.0 | 9.0 | 2.0 |
| 6l$_3$ | 2.000 | 0.0 | 0.0 | 4.0 | 0.0 | 0.0 | 9.0 |  | 6.0 | 8.0 | 6.0 | 8.0 |
|  | 1.000 | 0.0 | 0.0 | 3.0 | 0.0 | 0.0 | 0.0 |  | 5.0 | 6.0 | 4.0 | 6.0 |
|  | .500 | 0.0 | 0.0 | 1.0 | 0.0 | 0.0 | 1.0 |  | 5.0 | 5.0 | 3.0 | 4.0 |
| 6m$_3$ | 2.000 | 5.0 | 9.0 | 9.0 | 4.0 | 9.0 | 9.0 |  | 9.0 | 9.0 | 9.0 | 9.0 |
|  | 1.000 | 3.0 | 2.0 | 9.0 | 2.0 | 5.0 | 9.0 |  | 9.0 | 9.0 | 8.0 | 9.0 |
|  | .600 |  |  |  |  |  |  | 8.0 | 9.0 | 9.0 | 7.0 | 9.0 |
|  | .500 | 0.0 | 0.0 | 9.0 | 0.0 | 2.0 | 9.0 |  | 9.0 | 9.0 | 8.0 | 9.0 |
| 6n$_3$ | 4.000 | 4.0 | 7.0 | 9.0 | 4.0 | 9.0 | 9.0 |  | 9.0 | 9.0 | 9.0 | 9.0 |
|  | 2.000 | 3.0 | 5.0 | 9.0 | 4.0 | 9.0 | 9.0 |  | 9.0 | 9.0 | 9.0 | 9.0 |
|  | 1.000 | 1.0 | 3.0 | 9.0 | 1.0 | 9.0 | 9.0 |  | 9.0 | 9.0 | 9.0 | 9.0 |
|  | .600 |  |  |  |  |  |  | 9.0 | 9.0 | 9.0 | 7.0 | 9.0 |
|  | .500 | 0.0 | 0.0 | 9.0 | 0.0 | 9.0 | 9.0 |  | 9.0 | 8.0 | 7.0 | 9.0 |
| 6p$_3$ | 4.000 | 5.0 | 4.0 | 8.0 | 6.0 | 8.0 | 9.0 | 9.0 | 9.0 | 8.0 | 9.0 |  |
|  | 2.000 | 3.0 | 1.0 | 9.0 | 1.0 | 8.0 | 8.0 |  | 9.0 | 9.0 | 7.0 | 9.0 |
|  | 1.000 | 1.0 | 0.0 | 7.0 | 5.0 | 2.0 | 5.0 |  | 9.0 | 9.0 | 9.0 | 9.0 |
|  | .500 | 4.0 | 0.0 | 5.0 | 5.0 | 2.0 | 4.0 |  | 9.0 | 9.0 | 3.0 | 8.0 |
| 6q$_3$ | 4.000 | 0.0 | 0.0 | 2.0 | 0.0 | 1.0 | 0.0 |  | 3.0 | 2.0 | 0.0 | 8.0 |
|  | .500 | 0.0 | 0.0 | 0.0 | 0.0 | 0.0 | 6.0 |  | 7.0 | 2.0 | 0.0 | 1.0 |
| 6r$_3$ | 4.000 | 0.0 | 0.0 | 1.0 | 0.0 | 2.0 | 0.0 |  | 3.0 | 1.0 | 0.0 | 1.0 |
|  | .500 | 0.0 | 0.0 | 0.0 | 0.0 | 0.0 | 0.0 |  | 5.0 | 0.0 | 0.0 | 0.0 |
| 6s$_3$ | 4.000 | 0.0 | 0.0 | 0.0 | 0.0 | 0.0 | 0.0 |  | 5.0 | 1.0 | 0.0 | 1.0 |

| Compound of Example | RATE | BARNY ARDGR | FOXTA IL SP | P NUT SEDGE | WILD OATS | QUACK GRASS | FLD B INDWD | MRNGL RY SP | WILD MUSTD | RAGWE ED | VELVE TLEAF |
|---|---|---|---|---|---|---|---|---|---|---|---|
| 10b | 4.000 | 0.0 | 0.0 | 4.0 | 0.0 | 0.0 | 3.0 | 6.0 |  | 8.0 | 9.0 |
|  | 2.000 | 1.0 | 0.0 | 4.0 | 1.0 | 1.0 | 3.0 | 6.0 |  | 6.0 | 8.0 |
|  | 1.000 | 0.0 | 0.0 | 1.0 | 0.0 | 0.0 | 1.0 | 3.0 |  | 6.0 | 7.0 |
|  | .500 | 0.0 | 0.0 | 0.0 | 0.0 | 0.0 | 0.0 | 1.0 |  | 5.0 | 6.0 |
| 10c | 4.000 | 0.0 | 0.0 | 0.0 | 0.0 | 0.0 | 0.0 | 2.0 |  | 1.0 | 4.0 |
|  | 2.000 | 0.0 | 0.0 | 0.0 | 0.0 | 0.0 | 0.0 | 2.0 |  | 0.0 | 3.0 |
|  | 1.000 | 0.0 | 0.0 | 0.0 | 0.0 | 0.0 | 0.0 | 2.0 |  | 0.0 | 0.0 |
|  | .500 | 0.0 | 0.0 | 0.0 | 0.0 | 0.0 | 0.0 | 1.0 |  | 0.0 | 0.0 |
| 10d | 4.000 | 0.0 | 1.0 | 0.0 | 0.0 | 0.0 | 1.0 | 6.0 |  | 6.0 | 7.0 |
|  | 2.000 | 0.0 | 0.0 | 0.0 | 0.0 | 0.0 | 0.0 | 2.0 |  | 4.0 | 4.0 |
|  | 1.000 | 0.0 | 0.0 | 0.0 | 0.0 | 0.0 | 0.0 | 1.0 |  | 2.0 | 3.0 |
|  | .500 | 0.0 | 0.0 | 0.0 | 0.0 | 0.0 | 0.0 | 1.0 |  | 1.0 | 1.0 |
| 10e | 4.000 | 0.0 | 0.0 | 0.0 | 0.0 | 4.0 | 9.0 | 8.0 |  | 8.0 | 8.0 |
|  | 2.000 | 0.0 | 0.0 | 0.0 | 0.0 | 2.0 | 2.0 | 7.0 |  | 4.0 | 7.0 |
|  | 1.000 | 0.0 | 0.0 | 0.0 | 0.0 | 0.0 | 1.0 | 1.0 |  | 1.0 | 2.0 |
|  | .500 | 0.0 | 0.0 | 0.0 | 0.0 | 0.0 | 0.0 | 0.0 |  | 0.0 | 4.0 |
| 10f | 4.000 | 0.0 | 0.0 | 0.0 | 0.0 | 4.0 | 5.0 | 0.0 |  | 6.0 | 6.0 |
|  | 2.000 | 0.0 | 0.0 | 0.0 | 0.0 | 0.0 | 0.0 | 0.0 |  | 3.0 | 7.0 |
|  | 1.000 | 0.0 | 0.0 | 0.0 | 0.0 | 0.0 | 0.0 | 0.0 |  | 3.0 | 0.0 |
|  | .500 | 0.0 | 0.0 | 0.0 | 0.0 | 0.0 | 0.0 | 0.0 |  | 2.0 | 0.0 |
| 10g | 4.000 | 0.0 | 2.0 | 0.0 | 0.0 | 2.0 | 2.0 | 5.0 |  | 6.0 | 8.0 |
|  | 2.000 | 0.0 | 0.0 | 0.0 | 0.0 | 2.0 | 0.0 | 1.0 |  | 5.0 | 7.0 |
|  | 1.000 | 0.0 | 0.0 | 0.0 | 0.0 | 0.0 | 0.0 | 0.0 |  | 2.0 | 6.0 |
|  | .500 | 0.0 | 0.0 | 0.0 | 0.0 | 0.0 | 0.0 | 0.0 |  | 0.0 | 5.0 |
| 10h | 4.000 | 3.0 | 3.0 | 6.0 | 3.0 | 6.0 | 6.0 | 6.0 | 9.0 | 9.0 | 9.0 |
|  | 2.000 | 2.0 | 3.0 | 2.0 | 2.0 | 4.0 | 7.0 | 7.0 | 8.0 | 8.0 | 8.0 |
|  | 1.000 | 1.0 | 1.0 | 0.0 | 1.0 | 2.0 | 1.0 | 4.0 | 6.0 | 6.0 | 7.0 |
|  | .500 | 0.0 | 0.0 | 0.0 | 0.0 | 1.0 | 0.0 | 2.0 | 6.0 | 6.0 | 7.0 |
| 10i | 4.000 | 4.0 | 6.0 | 3.0 | 1.0 | 7.0 | 7.0 | 7.0 | 7.0 | 7.0 | 8.0 |
|  | 2.000 | 4.0 | 5.0 | 3.0 | 1.0 | 7.0 | 7.0 | 6.0 | 8.0 | 7.0 | 8.0 |
|  | 1.000 | 2.0 | 4.0 | 2.0 | 1.0 | 7.0 | 5.0 | 5.0 | 7.0 | 7.0 | 7.0 |
|  | .500 | 1.0 | 3.0 | 1.0 | 1.0 | 4.0 | 5.0 | 3.0 | 7.0 | 6.0 | 6.0 |
| 10j | 2.000 | 0.0 | 0.0 | 0.0 | 0.0 | 0.0 | 0.0 | 1.0 | 8.0 | 7.0 | 7.0 |
|  | 1.000 | 0.0 | 0.0 | 0.0 | 0.0 | 0.0 | 0.0 | 1.0 | 2.0 | 6.0 | 4.0 |
|  | .500 | 0.0 | 0.0 | 0.0 | 0.0 | 0.0 | 0.0 | 0.0 | 3.0 | 7.0 | 5.0 |
| 10k | 4.000 | 5.0 | 9.0 | 6.0 | 2.0 | 9.0 | 9.0 | 7.0 | 9.0 | 9.0 | 9.0 |
|  | 2.000 | 5.0 | 6.0 | 6.0 | 1.0 | 9.0 | 9.0 | 6.0 | 9.0 | 9.0 | 9.0 |

TABLE VII-continued
PRE-EMERGENCE TESTS - RATES IN KG/HA
|     |       |     |     |     |     |     |     |     |     |     |     |
|-----|-------|-----|-----|-----|-----|-----|-----|-----|-----|-----|-----|
|     | 1.000 | 4.0 | 4.0 | 6.0 | 1.0 | 5.0 | 5.0 | 5.0 | 9.0 | 9.0 | 9.0 |
|     | .500  | 4.0 | 3.0 | 5.0 | 0.0 | 6.0 | 5.0 | 6.0 | 9.0 | 9.0 | 8.0 |
| 10l | 4.000 | 0.0 | 1.0 | 0.0 | 0.0 | 0.0 | 0.0 | 0.0 | 0.0 | 0.0 | 0.0 |
| 10m | 4.000 | 0.0 | 0.0 | 0.0 | 0.0 | 0.0 | 7.0 | 3.0 | 4.0 | 6.0 | 6.0 |
|     | 2.000 | 0.0 | 0.0 | 0.0 | 0.0 | 0.0 | 6.0 | 5.0 | 4.0 | 5.0 | 5.0 |
|     | 1.000 | 0.0 | 0.0 | 0.0 | 0.0 | 0.0 | 0.0 | 1.0 | 1.0 | 2.0 | 3.0 |
|     | .500  | 0.0 | 0.0 | 0.0 | 0.0 | 0.0 |     | 0.0 | 0.0 | 2.0 | 2.0 |
| 10n | 4.000 | 5.0 | 6.0 | 9.0 | 6.0 | 9.0 | 9.0 | 7.0 | 9.0 | 9.0 | 9.0 |
|     | .500  | 0.0 | 8.0 | 9.0 | 1.0 | 9.0 | 9.0 | 4.0 | 9.0 | 9.0 | 7.0 |
| 10o | 4.000 | 0.0 | 5.0 | 5.0 | 2.0 | 8.0 | 8.0 | 6.0 | 6.0 | 9.0 | 9.0 |
|     | .500  | 0.0 | 0.0 | 8.0 | 0.0 | 6.0 | 0.0 | 5.0 | 5.0 | 0.0 | 6.0 |
| 10p | 4.000 | 0.0 | 0.0 | 0.0 | 0.0 | 0.0 | 1.0 | 1.0 | 7.0 | 0.0 | 5.0 |
|     | .500  | 0.0 | 0.0 | 0.0 | 0.0 | 2.0 | 0.0 | 0.0 | 2.0 | 0.0 | 1.0 |
| 11a | 4.000 | 1.0 | 0.0 | 6.0 | 3.0 | 9.0 | 8.0 | 5.0 | 9.0 | 7.0 | 8.0 |
|     | .500  | 0.0 | 0.0 | 3.0 | 1.0 | 6.0 | 2.0 | 2.0 | 9.0 | 1.0 | 7.0 |
| 11b | 4.000 | 1.0 | 2.0 | 6.0 | 3.0 | 6.0 | 9.0 | 7.0 | 7.0 | 7.0 | 7.0 |
|     | .500  | 0.0 | 0.0 | 2.0 | 1.0 | 4.0 | 8.0 | 6.0 | 4.0 | 2.0 | 1.0 |
| 11c | 4.000 | 1.0 | 1.0 | 3.0 | 1.0 | 9.0 | 8.0 | 4.0 | 8.0 | 3.0 | 7.0 |
|     | .500  | 0.0 | 0.0 | 1.0 | 0.0 | 4.0 | 1.0 | 0.0 | 2.0 | 0.0 | 1.0 |
| 11d | 4.000 | 0.0 | 0.0 | 6.0 | 0.0 | 4.0 | 3.0 | 4.0 | 8.0 | 6.0 | 7.0 |
|     | .500  | 0.0 | 0.0 | 0.0 | 0.0 | 0.0 | 0.0 | 0.0 | 0.0 | 0.0 | 2.0 |
| 11e | 4.000 | 0.0 | 0.0 | 0.0 | 0.0 | 3.0 | 7.0 | 7.0 | 3.0 | 1.0 | 2.0 |
|     | .500  | 0.0 | 0.0 | 0.0 | 0.0 | 0.0 | 0.0 | 0.0 | 0.0 | 0.0 | 1.0 |
| 11f | 4.000 | 0.0 | 0.0 | 6.0 | 0.0 | 9.0 | 9.0 | 6.0 | 5.0 | 9.0 | 7.0 |
|     | .500  | 0.0 | 0.0 | 0.0 | 0.0 | 2.0 | 3.0 | 0.0 | 0.0 | 0.0 | 3.0 |
| 11g | 4.000 | 3.0 | 1.0 | 6.0 | 1.0 | 9.0 | 5.0 | 5.0 | 6.0 | 7.0 | 7.0 |
|     | .500  | 0.0 | 0.0 | 0.0 | 0.0 | 3.0 | 2.0 | 3.0 | 2.0 | 2.0 | 5.0 |
| 11h | 4.000 | 0.0 | 0.0 | 0.0 | 0.0 | 0.0 | 3.0 | 2.0 | 7.0 | 3.0 | 0.0 |
| 11i | 4.000 | 0.0 | 0.0 | 7.0 | 0.0 | 4.0 | 9.0 | 7.0 | 9.0 | 6.0 | 7.0 |
|     | .500  | 0.0 | 0.0 | 0.0 | 0.0 | 0.0 | 4.0 | 4.0 | 0.0 | 0.0 | 2.0 |
| 18a | 4.000 | 5.0 | 8.0 | 9.0 | 7.0 | 9.0 | 9.0 | 7.0 | 9.0 | 9.0 | 9.0 |
|     | 2.000 | 4.0 | 5.0 | 9.0 | 4.0 | 9.0 | 9.0 | 8.0 | 9.0 | 9.0 | 9.0 |
|     | 1.000 | 0.0 | 0.0 | 8.0 | 3.0 | 7.0 | 6.0 | 6.0 | 9.0 | 7.0 | 7.0 |
|     | .500  | 0.0 | 0.0 | 6.0 | 0.0 | 2.0 | 7.0 | 5.0 | 9.0 | 6.0 | 7.0 |
| 19a | 4.000 | 5.0 | 4.0 | 9.0 | 4.0 | 9.0 | 9.0 | 9.0 | 9.0 | 9.0 | 9.0 |
|     | 2.000 | 1.0 | 1.0 | 9.0 | 1.0 | 3.0 | 9.0 | 9.0 | 9.0 | 7.0 | 9.0 |
|     | 1.000 | 0.0 | 0.0 | 9.0 | 2.0 | 4.0 | 9.0 | 9.0 | 9.0 | 8.0 | 9.0 |
|     | .500  | 0.0 | 0.0 | 9.0 | 0.0 | 2.0 | 9.0 | 9.0 | 9.0 | 6.0 | 9.0 |
| 20a | 4.000 | 3.0 | 4.0 | 9.0 | 3.0 | 9.0 | 9.0 | 7.0 | 9.0 | 9.0 | 9.0 |
|     | 2.000 | 2.0 | 6.0 | 9.0 | 1.0 | 9.0 | 9.0 | 7.0 | 9.0 | 6.0 | 9.0 |
|     | 1.000 | 1.0 | 3.0 | 9.0 | 1.0 | 9.0 | 9.0 | 7.0 | 9.0 | 7.0 | 8.0 |
|     | .500  | 1.0 | 1.0 | 8.0 | 0.0 | 3.0 | 9.0 | 6.0 | 7.0 | 6.0 | 8.0 |
| 21a | 4.000 | 5.0 | 5.0 | 9.0 | 4.0 | 9.0 | 9.0 | 8.0 | 9.0 | 9.0 | 9.0 |
|     | 2.000 | 4.0 | 7.0 | 9.0 | 4.0 | 9.0 | 9.0 | 7.0 | 9.0 | 7.0 | 9.0 |
|     | 1.000 | 4.0 | 4.0 | 9.0 | 4.0 | 9.0 | 9.0 | 7.0 | 9.0 | 8.0 | 9.0 |
|     | .500  | 0.0 | 3.0 | 9.0 | 3.0 | 3.0 | 9.0 | 6.0 | 7.0 | 5.0 | 9.0 |
| 21b | 4.000 | 4.0 | 2.0 | 9.0 | 7.0 | 9.0 | 9.0 | 9.0 | 9.0 | 9.0 | 9.0 |
|     | 2.000 | 6.0 | 8.0 | 9.0 | 7.0 | 9.0 | 9.0 | 9.0 | 9.0 | 9.0 | 9.0 |
|     | 1.000 | 3.0 | 2.0 | 9.0 | 5.0 | 9.0 | 7.0 | 9.0 | 9.0 | 9.0 | 8.0 |
|     | .500  | 5.0 | 3.0 | 9.0 | 5.0 | 9.0 | 8.0 | 8.0 | 9.0 | 9.0 | 8.0 |
| 21c | 4.000 | 0.0 | 0.0 | 9.0 | 1.0 | 5.0 | 9.0 | 8.0 | 7.0 | 4.0 | 5.0 |
|     | 2.000 | 0.0 | 0.0 | 4.0 | 0.0 | 0.0 | 7.0 | 8.0 | 7.0 | 6.0 | 6.0 |
|     | 1.000 | 0.0 | 0.0 | 4.0 | 0.0 | 0.0 | 9.0 | 7.0 | 6.0 | 3.0 | 6.0 |
|     | .500  | 0.0 | 0.0 | 4.0 | 0.0 | 0.0 | 3.0 | 6.0 | 5.0 | 1.0 | 3.0 |
What is claimed is:
1. Intermediates having the structures:
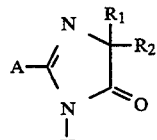
VII
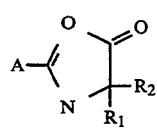
XV
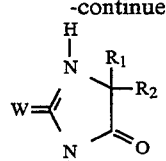
XVII
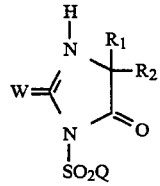
XVIII
wherein
A is hydrogen or methyl
$R_1$ is methyl;

$R_2$ is isopropyl;
W is oxygen or sulfur; and
Q is
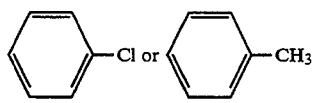
2. A compound according to claim 1, 4-isopropyl-2,4-dimethyl-2-oxazolin-5-one.
3. A compound according to claim 1, 5-isopropyl-5-methyl-3-(p-tolylsulfonyl)hydantoin.
* * * * *